United States Patent
Kruger et al.

[11] Patent Number: 5,352,364
[45] Date of Patent: Oct. 4, 1994

[54] MEDICAL DRUG FORMULATION AND DELIVERY SYSTEM AND REVERSE OSMOSIS PURIFICATION DEVICE

[75] Inventors: Robert J. Kruger, Arlington Heights; Warren P. Frederick, Wonder Lake; Mark E. Larkin, Lindenhurst; Joaquin Mayoral, Mundelein; Sheldon M. Wecker, Libertyville, all of Ill.

[73] Assignee: Abbott Laboratories, Abbott Park, Ill.

[21] Appl. No.: 990,580

[22] Filed: Dec. 15, 1992

Related U.S. Application Data

[62] Division of Ser. No. 570,660, Aug. 20, 1990, abandoned.

[51] Int. Cl.$^5$ ............................................. B01D 61/08
[52] U.S. Cl. .................................. 210/652; 210/259; 210/321.75
[58] Field of Search .............. 210/641, 652, 321.75, 210/259, 317, 257.2, 651; 604/4, 5, 6

[56] References Cited

U.S. PATENT DOCUMENTS

| | | | |
|---|---|---|---|
| T921,001 | 4/1974 | Devaney. | |
| 4,263,017 | 4/1981 | Karn | 210/321.75 X |
| 4,610,790 | 9/1986 | Reti et al. | 210/259 X |
| 4,990,248 | 2/1991 | Brown et al. | 210/317 X |
| 5,167,816 | 12/1992 | Kruger et al. | 210/257.2 |

Primary Examiner—Frank Spear
Attorney, Agent, or Firm—A. Nicholas Trausch

[57] ABSTRACT

A reverse osmosis device for purifying water from a source comprising a housing having an inlet for passage of water from the source, a first outlet for passage of purified water from the housing and a second outlet for passage of waste water remaining after purification. A first reverse osmosis multilayer assembly is disposed within the housing in fluid communication with the inlet for purification of at least a first portion of the water from the source. Water treatment chemicals can be positioned in a core about which the first reserve osmosis multilayer assembly is wound. The treatment chemicals are in fluid communication with the first reverse osmosis multilayer assembly to receive the first purified portion of water and for removal of at least chemical contaminants therefrom. A second reverse osmosis multilayer assembly is also wound on the core and is in fluid communication with the water treatment chemicals to receive the chemically purified water for purification of at least a second portion thereof. The second reserve osmosis multilayer assembly is in fluid communication with the first outlet so as to permit passage of the second portion of purified water therethrough.

5 Claims, 30 Drawing Sheets

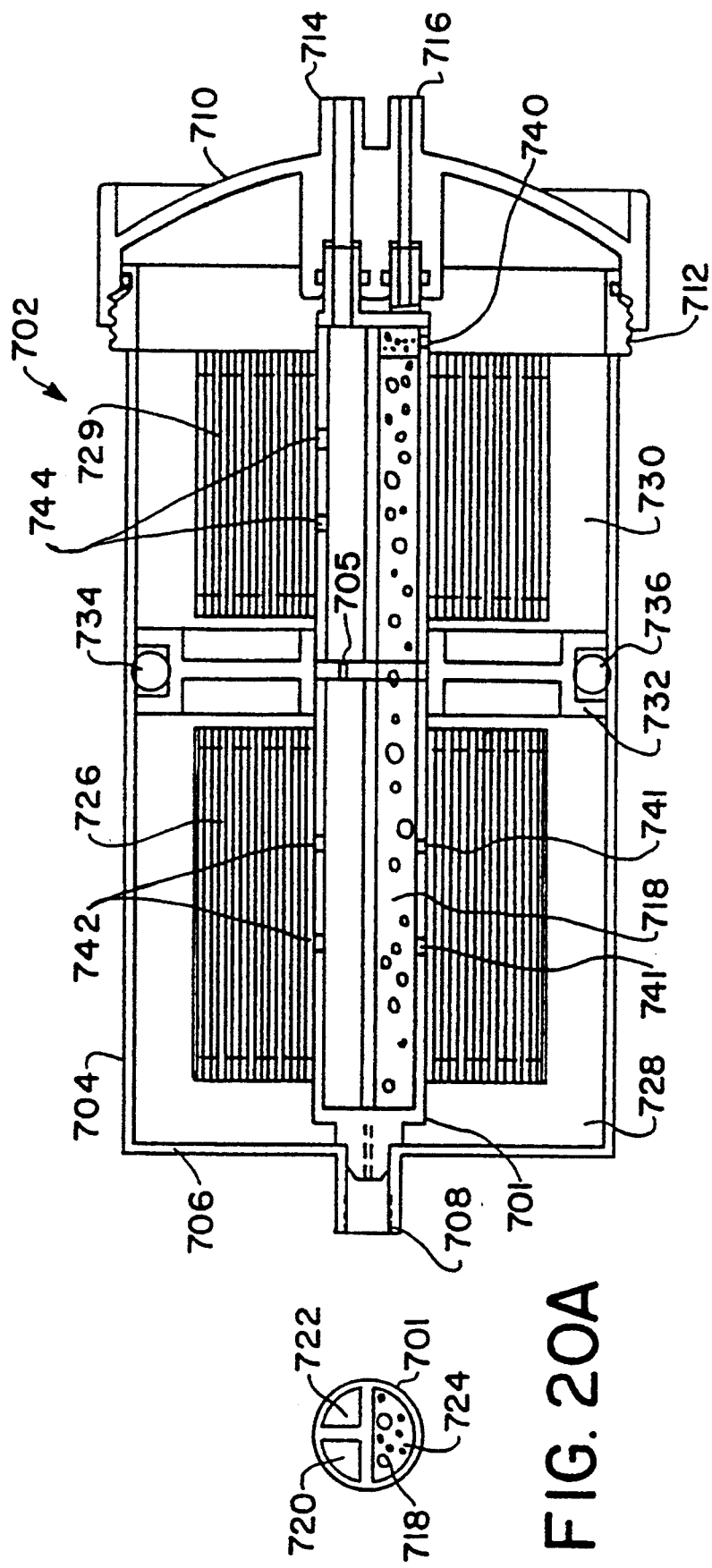

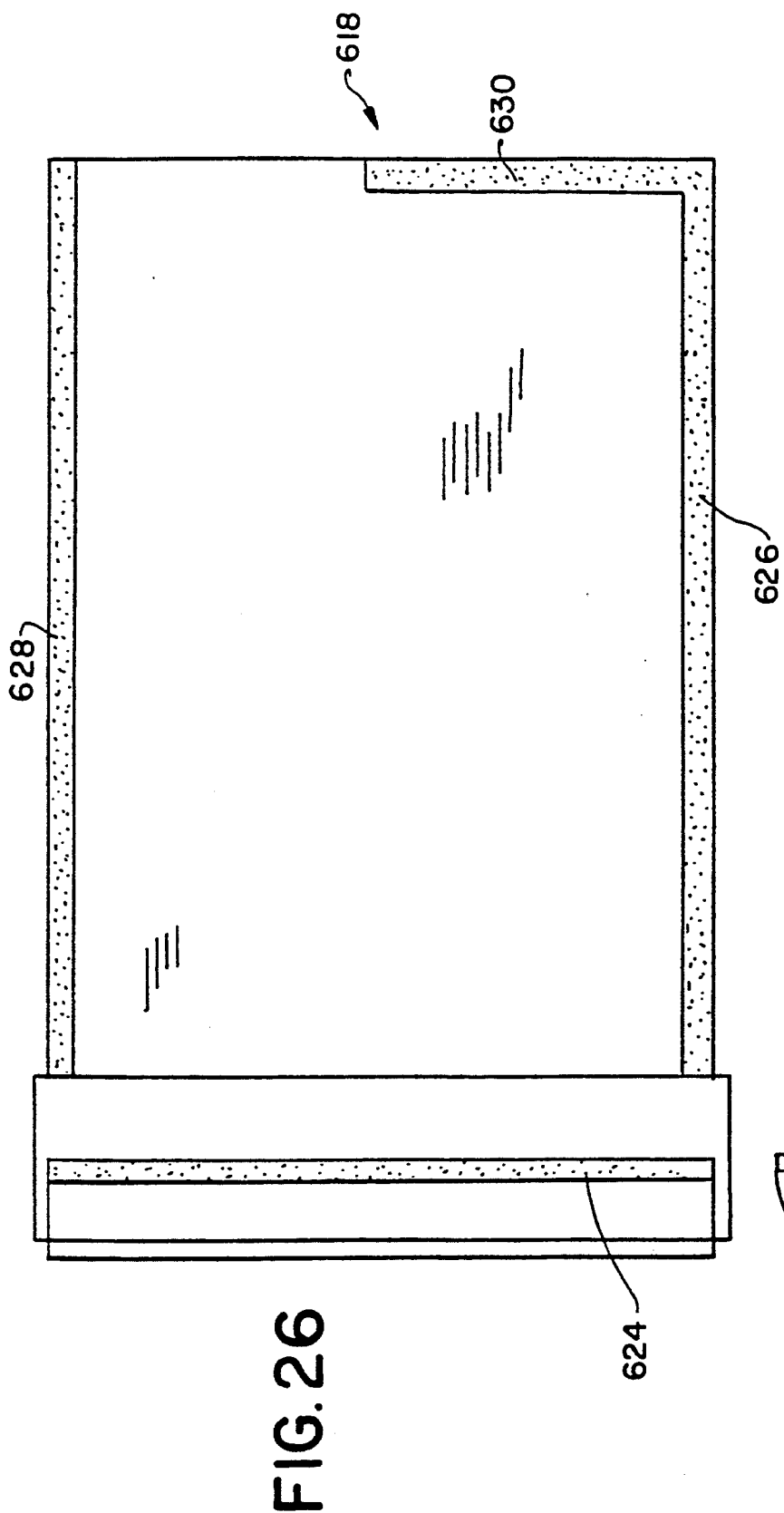
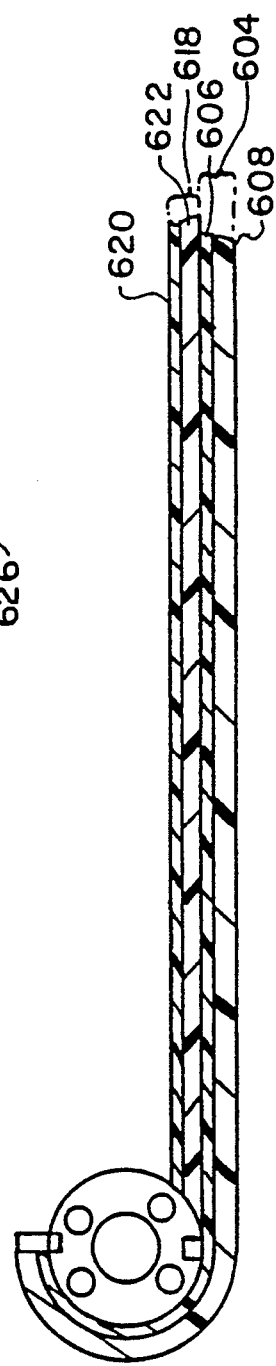
FIG.26
FIG.25

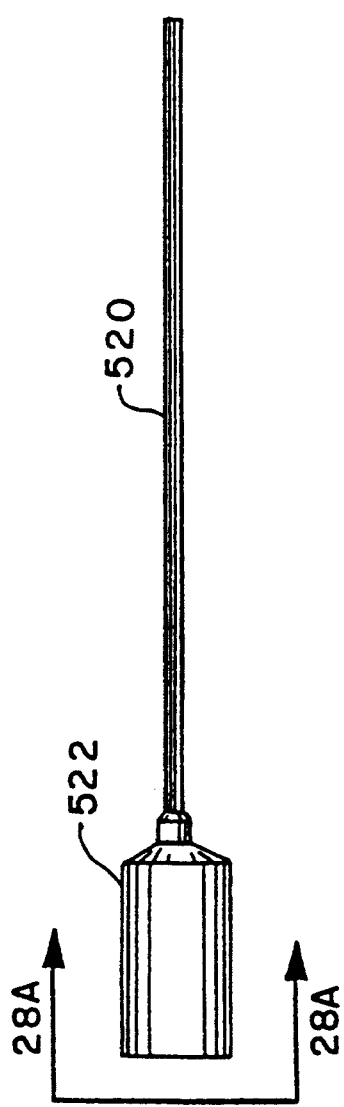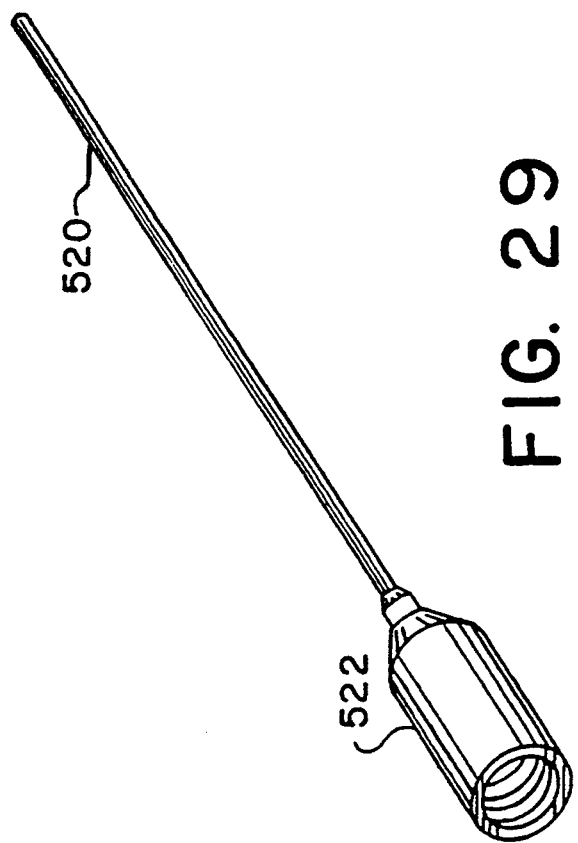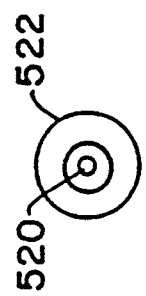
FIG. 28
FIG. 29
FIG. 28A

MEDICAL DRUG FORMULATION AND DELIVERY SYSTEM AND REVERSE OSMOSIS PURIFICATION DEVICE

This is a division of application Ser. No. 07/570,660, filed Aug. 20, 1990, now abandoned.

The present invention relates to a device for purifying fluids and in particular to a reverse osmosis device for use, for example, in sterilizing and purifying fluids serially through at least two reverse osmosis stages, for use in a system for medical drug formulation and delivery and for other end use applications.

BACKGROUND OF THE INVENTION

The purification or separation of fluids using synthetic membranes can be advantageously used in many industrial, medical and home applications. Typical membrane separation processes include gas and vapor diffusion, dialysis, ultrafiltration and reverse osmosis.

Synthetic polymeric membranes can be applied to gaseous systems to separate gaseous solutions into their components. The membrane used in the gaseous systems must be permeable and selective, possess chemical and physical stability and be free of structural irregularities such as pinholes. The containing vessel should be capable of supporting these membranes under large pressure differentials; have a large membrane surface area per unit volume; cause a minimum pressure drop in the gas streams; and be inexpensive, i.e., be constructed of low-cost materials which are easy to fabricate and assemble. An example of such gas separation using synthetic membranes is the recovery of helium from natural gas and of oxygen from air. Such membrane separation processes, however, are often not competitive to known cryogenic processes because of the high power requirements for membrane separation.

Synthetic polymeric membranes have been applied to dialysis wherein some solutes selectively permeate through the membrane based on the concentration gradient across the membrane. While the dialysis process is not particularly rapid, it has been industrially utilized, for example, in the recovery of caustic from rayon and the recovery of spent acid from metallurgical liquors.

Ultrafiltration typically involves the separation of large solute particles from the solvent of the solution by forcing the solvent to pass through a membrane while the particles are retained to a greater or lesser extent. Often the separation involves a physical sieving of the particles which are retained on top of the membrane filter. For membranes of low pore radius, however, the process of ultrafiltration begins to overlap the process of reverse osmosis wherein the physical sieving phenomena is increasingly replaced with the adsorption and solubility of the solute within the membrane. The retained solutes consequently can have significant osmotic pressures which must be overcome by higher fluid pressures.

Hemodialysis is an example of a dialysis process which is assisted by ultrafiltration. A hemodialyzer is a membrane-containing device which is able to remove certain waste products such as urea, creatinine and uric acid from the blood. The patient's blood is introduced into the hemodialyzer preferably under the patient's own perfusion pressure and flows past the membrane which is typically cellulose. The blood solutes containing the waste then permeate through the membrane and into the dialysate, a sterilized solution formulated to control solute permeability through the membrane. Because osmosis may result in the undesirable net transfer of water from the dialysate into the blood which may result in edema, hemodialysis is often utilized in conjunction with ultrafiltration to remove the excess water. The dialysate can be prepared by the combination of purified water, produced by reverse osmosis, and the desired concentrate.

Reverse osmosis using synthetic polymeric membranes has been used for a variety of industrial end products. Such processes include the desalination of sea water and the processing of food and beverages. The alternative method of processing is by distillation. However, because of the high energy requirements of distillation, reverse osmosis processes compare favorably as the most economic route. Furthermore, for solutions susceptible to degradation at high temperatures such as fruit juices, reverse osmosis may be the most practical manner of processing the solutions while preventing substantial loss of desirable components in the original solutions.

An important use of the reverse osmosis process in the medical field is its application to peritoneal dialysis therapy. A generalized discussion of peritoneal dialysis therapy is discussed and described in U.S. Pat. No. 4,239,041 to Popovich et al. In particular, the Popovich patent discusses a fluid infusion method for continuous, ambulatory peritoneal dialysis (CAPD). The CAPD process differs from the more popular hemodialysis process in that it utilizes the body's natural peritoneal membrane in order to provide for the function of the artificial kidney. The CAPD process, however, while being ambulatory, is performed during the patient's normal, daily routine and requires treatment several times during the day. For this reason, the patient must remain by the dialysate supply during the entire period of treatment. This obviously will conflict with the patient's daytime activities and/or job requirements.

Alternatively, peritoneal dialysis can be performed at a hospital or clinic which requires that the patient visit the facility in order to obtain the required treatment. Such a visit requirement also has its inherent limitations on the normal activities of the patient.

Peritoneal dialysis is also generally discussed and described in the "Handbook 6010, Automated Peritoneal Dialysis", 1979 which is incorporated herein by reference. This handbook was distributed by B-D Drake Willock, a division of Becton, Dickenson and Co. in New Jersey and discusses that dialysate which is prepared from purified water can be infused into the patient's peritoneum through a catheter. Dialysis of the patient's blood through the peritoneal membrane and into the purified water region then occurs, allowing the body to excrete water, metabolites and toxins, and to regulate fluid, electrolyte and acid-base balance. The waste dialysate is subsequently drained out of the body. Peritoneal dialysis can be performed by various methods such as continuous and intermittent, as explained in Miller et al. "Automated Peritoneal Dialysis Analysis of Several Methods of Peritoneal Dialysis", Vol. XII Trans. Amer. Soc. Artif. Int. Organs p. 98 (1966).

Problems related to peritoneal dialysis include the difficulty in maintaining sterile conditions so as to prevent infection and the complexity of operating currently available peritoneal dialysis systems. A peritoneal dialysis device manufactured by Physio-Control Corporation of Redmond, Washington is generally described in "PDS 400 Service Manual P/N 10454–01 July, 1981"

which is also incorporated herein by reference. The device purifies the source water using a reverse osmosis module which is formed of a plastic housing containing a spiral wound membrane of cellulose triacetate. The device mixes the purified water with concentrate to form a dialysate, and then delivers the dialysate to the patient. The system controls the dialysate delivery at a set inflow rate and period and a set outflow period. An alarm is sounded and the system is turned off if various parameters are not within the set ranges. The parameters include the dialysate temperature, the dialysate conductivity, the inflow and outflow volume, and the system overpressure. The Physio-Control device is made up of two subsystems; the RO unit and the proportioning and monitoring unit. The device is bulky and complex in operation and requires extensive training of either the medical personnel or the patient that operate it. Additionally, extensive preventive maintenance is required to keep the system operational. Such maintenance includes the replacement of the RO pre-filter, filters and O-rings within the device every 500 hours of use as well as the cleaning of the RO sump pump. In addition, the device requires cleansing with bleach every 100 hours. Moreover, an extensive disinfection with formaldehyde must be performed before patient use if the sterile path has been broken during the functional test, calibration or adjustment of the device.

Another peritoneal dialysis device was designed by Ramot Purotech Ltd. The device employs RO membrane filtration through an RO cell formed of a large number of small membranes supported on plastic plates. After mixing the filtered water with concentrate to form the dialysate, the dialysate is fed by gravity to the patient. The outflow from the patient is also done by gravity into a waste bag. The need to connect the dialysate to the patient, leads to difficulties in maintaining sterile conditions.

Yet another peritoneal dialysis system is disclosed in U.S. Pat. No. 4,586,920; 4,718,890; and 4,747,822 to Peabody. The patents recite a continuous flow peritoneal dialysis system and process in which a continuous flow of sterile dialysis fluid is produced and caused to flow through the peritoneal cavity of the patient is a single-pass open circuit. A gravity fed system is utilized to flow the fluid into the patient's peritoneum. The pressure of the peritoneum and the volume of fluid into the peritoneum are monitored to ensure efficient and comfortable peritoneal dialysis. The pressure monitors of the system are capable of controlling the flow of fluid into the peritoneum. This system, however similar to others previously discussed, does not address the manner in which sterile conditions may maintained nor the daunting complexity of operation required to be performed by the patient or care giver to use and maintain the system.

These and other problems have been solved in part by another device for peritoneal dialysis treatment called eco. the Inpersol Cycler TM 1000, the Handbook of which is incorporated herein by reference. The Cycler TM is used to perform peritoneal dialysis in continuous cycling peritoneal dialysis (CCPD) and intermittent peritoneal dialysis (IPD) applications. The Cycler TM 3000 is used to not only perform CCPD and IPD but also tidal peritoneal dialysis (TPD). The Cycler TM is portable and is designed to be used in the home as well as in the clinic or hospital. In typical CCPD applications the exchanges are made at night while the patient is sleeping. A portion of the final dose is retained in the peritoneum during the day and drained out at beginning of the nightly exchanges. The cycler system includes the cycler control unit and the stand. The stand holds the cycler unit, and fresh and spent dialysis fluids. The cycler control unit contains the wagoner, weighing system, valving system and control electronics.

Notwithstanding the Cycler TM, the problems of other known peritoneal dialysis devices have been solved by the present invention which is directed to a reverse osmosis (RO) filtration device for purifying water and for use in a user friendly automatic home dialysis system which will permit the patient to obtain peritoneal dialysis during sleeping hours. In this fashion, the patient will be free to conduct his normal activities during his waking or business hours without the interference of dialysis treatment. Additionally, the RO device and system of the present invention provide a self-contained, compact and sophisticated system whereby peritoneal dialysis is automatically performed and continuously controlled so as to allow the patient to undergo peritoneal dialysis at home with minimal need for patient intervention. This permits the patient to lead a more natural and fuller life than permitted under known treatment procedures.

The RO device and system of the present invention also provide for a low cost, efficient means to produce solutions of sufficient sterility, low pyrogen content and low dissolved mineral content for many other industrial and medical applications. Because of the compactness of the apparatus and its ease of use, purified fluids such as sterile and pyrogen-free water can be produced on site as needed without the inconvenience and cost of storing large quantities of the purified fluid. When applied to purifying water, the invention produces water of sufficient sterility such that the purified water can be employed in peritoneal dialysis, irrigation of patients during surgery or postoperative therapy, and pharmaceutical production for oral and intravenous administration. Additionally, the RO device can produce sterile water for the formulation of dialysate solution required in hemodialysis treatment. The purified water as produced by the device and system of the present invention can satisfy U.S.P. requirements as presented in the United States Pharmacopeia, The National Formulary P1456-1574, 1596-1598, 1705-1710, Jan. 1, 1990, US PXXII United States Pharmacopeial Convention, Inc. Also, the RO device and system avoids any need for terminal sterilization as required by known peritoneal dialysis devices.

Alternatively, the RO device and system of the present invention may be adapted to supply sterile water for the formulation of dialysate for use in hemodialyzers. The hemodialyzers in turn use the dialysate to purify the patient's blood in a manner currently used in hospitals and clinics.

For less demanding processes where sterility is not a major concern, the RO device and/or system of the present invention may be adapted to dialysis and ultrafiltration processes. Typical end use applications include those previously discussed such as the recovery of spent caustic or acid solutions from industrial production liquors (i.e. rayon steep liquor and metallurgical liquor).

The present invention is also directed toward the method of manufacturing the RO device in a manner which would minimize the cost of manufacturing and expedite it as well. Assembly steps include the application of adhesive in an automated manner by roller coating, induction bonding, sonic welding, and radiation sterilization.

SUMMARY OF THE INVENTION

The present invention is directed to an apparatus for purifying fluid from a source comprising first reverse osmosis means adapted for fluid communication with the source for purification of at least a portion of the fluid from the source; and second reverse osmosis means being in fluid communication with the first reverse osmosis means to receive at least some of the purified portion of fluid for further purification of at least a further portion of the fluid.

The fluid may be in the liquid or gaseous state. The configuration of the reverse osmosis means includes reverse osmosis multilayer assemblies which are either spirally wound or stacked in a parallel leaf configuration. Alternatively, the reverse osmosis means is in the form of hollow non-porous semipermeable membrane fibers composed of synthetic merane. Synthetic membranes useful for reverse osmosis include cellulose nitrate, cellulose acetate, polyamides, polyimides, polytetrafluoroethylene, poly-(vinyl chloride) and polysulfone.

Preferably the RO apparatus is for use with a potable water source and the first reverse osmosis means comprises a first reverse osmosis multilayer assembly spirally rolled about a first axis so as to provide a generally spiral flow path of the water from the source. The second reverse osmosis multilayer assembly is spirally rolled about a second axis so as to provide a generally spiral flow path for at least some of the purified first portion of water from the first reverse osmosis means.

Preferably, the first and said second reverse osmosis multilayer assemblies are formed integrally and the first axis and the second axis are co-linear. A separator means is disposed so as to fluidly separate the integral multilayer assembly when rolled about its axis into the first and the second reverse osmosis multilayer assemblies.

In one embodiment, the separator means is an impermeable adhesive. Also the integral multilayer assembly comprises first reverse osmosis membrane layer; porous mesh layer; second reverse osmosis membrane layer; and porous permeate layer. A container can enclose either the first or the second reverse osmosis multilayer assembly.

In an alternative embodiment, the first reverse osmosis means is disposed in an interleaf configuration with the second reverse osmosis means and each comprises at least a reverse osmosis multilayer assembly spirally rolled about a common axis. Preferably, the first reverse osmosis multilayer assembly comprises first reverse osmosis membrane layer; porous mesh layer; second reverse osmosis membrane layer; and first porous permeate layer. The second reverse osmosis multilayer assembly comprises third reverse osmosis membrane layer; second porous permeate layer; fourth reverse osmosis membrane layer; and third porous permeate layer.

The present invention is also directed to a method for purifying fluid from a source comprising passing fluid from the source through a first reverse osmosis means being in fluid communication with the source so as to purify at least a portion of the fluid from the source; and passing the purified first portion of fluid through a second reverse osmosis means being in fluid communication with the first reverse osmosis means to receive the purified portion of water for further purification of the fluid. Preferably the fluid can be water.

According to another embodiment, the present invention is directed to an apparatus for purifying water from a source comprising housing having an inlet for passage of water from a source, a first outlet for passage of purified water from the housing and a second outlet for passage of waste water remaining after purification; first reverse osmosis means disposed within said housing and being in fluid communication with the inlet for purification of at least a first portion of the water from the source; the first reverse osmosis means also being in fluid communication with the second outlet for passage of waste water through the second outlet; chemical purification means being in fluid communication with the first reverse osmosis means to receive the first purified portion of water and for removal of at least chemical contaminants from the first purified portion of water; and second reverse osmosis means being in fluid communication with the chemical means to receive the chemically purified water for purification of at least a second portion of the chemically purified water, the second reverse osmosis means also being in fluid communication with the first outlet so as to permit passage of the second portion of purified water through the first outlet.

In one embodiment, the housing further comprises a third outlet for passage of waste water remaining after purification, and the first reverse osmosis means is in fluid communication with the third outlet so as to permit passage of waste water through the third outlet. The second reverse osmosis means is in fluid communication with the second outlet so as to permit passage of waste water through the second outlet.

The housing is formed of a material possessing sufficient structural integrity to withstand the pressure requirements of the reverse osmosis process. The material may be but is not limited to steel, aluminum, fiberglass and Kevlar TM . Also, the housing includes an elongated hollow cylindrical container having a base and an open end and includes a cap configured and dimensioned to seal the open end in a fluid tight configuration. The cap has an inlet passageway for admitting water from the source, a first passageway for purified water and a second passageway for waste water. A third outlet passageway could also be provided for passage of waste water. A generally cylindrical core is disposed within the housing and extends from the base to the cap. The integral multilayer assembly is rolled about the outer surface of the cylindrical core so as to provide for spiral flow paths of the water to be purified. The cylindrical core has a hollow central portion and the chemical means is disposed within the hollow central portion. The chemical means includes but is not limited to diatomaceous earth, clay, ion exchange resins, activated carbon or other similar material and mixtures thereof. The chemical means provides a variety of functions including the removal of dissolved gases and chloramine contaminants. Filter plugs are disposed at the ends of the hollow central portion so as to contain the chemical means therebetween. The apparatus further comprises a second cylindrical hollow container having a base and an open end and is configured and dimensioned so as to be adapted to be positioned within the first container and to receive and to seal the second reverse osmosis means therein. At least one 0 ring or other sealing means is disposed between the open end of the second cylindrical hollow container and the impermeable adhesive disposed along the central portion of the integral multilayer assembly so as to aid in sealing the first osmosis means within the second container.

Preferably, the integral multilayer assembly comprises first reverse osmosis membrane layer; porous mesh layer; second reverse osmosis-membrane layer; and porous permeate layer. Also, the first and said second reverse osmosis membrane layers each comprises nonporous semipermeable membrane layer; porous ultrafiltration layer; and porous support layer. The semipermeable membrane layer is formed generally of a solid nonporous continuous thin polymeric composition and the porous support layer is formed generally of polyamide which can be either of a woven or non-woven configuration.

After being rolled about the outer surface of the cylindrical core, the reverse osmosis multilayer assembly generally includes in a radially outwardly configuration from the surface, the porous permeate layer, the second reverse osmosis membrane layer, the porous mesh layer and the first reverse osmosis membrane layer. Preferably, the nonporous semi-permeable membrane layers of the first and the second reverse osmosis membrane layers are disposed adjacent the porous mesh layer.

In another preferred embodiment of the present invention, the apparatus has a second reverse osmosis means being in fluid communication with the first reverse osmosis means to receive the first purified portion of water for purification of at least a second portion of the purified water, the second reverse osmosis means also being in fluid communication with the second outlet for passage of waste water through the second outlet. Chemical means in fluid communication with the second reverse osmosis means receives the second purified portion of water and removes at least chemical contaminants from the second purified portion of water. The chemical means is also in fluid communication with the first outlet so as to permit passage of the second portion of purified water through the first outlet.

In another embodiment, the first reverse osmosis means is disposed in an interleaf configuration with the second reverse osmosis means. The first reverse osmosis means comprises at least a first reverse osmosis multilayer assembly and the second reverse osmosis means comprises at least a second reverse osmosis multilayer assembly. Both the first and the second reverse osmosis multilayer assemblies are spirally rolled about a common axis. The first reverse osmosis multilayer assembly comprises first reverse osmosis membrane layer; porous mesh layer; second reverse osmosis membrane layer; and first porous permeate layer. Also, the second reverse osmosis multilayer assembly comprises third reverse osmosis membrane layer; second porous permeate layer; fourth reverse osmosis membrane layer; and third porous permeate layer.

Preferably, the first, second, third and fourth reverse osmosis membrane layers each comprises nonporous semi-permeable membrane layer; porous ultrafiltration layer; and porous support layer. The semi-permeable merane layer is formed generally of a solid nonporous continuous thin polymeric composition such as polyamide. The porous support layer can be made of polyamide. The polyamide can be of a woven or non-woven configuration.

After the reverse osmosis multilayer assemblies are rolled about the outer surface of the cylindrical core, they include in a radially outwardly configuration from the surface, the third porous permeate layer, the fourth reverse osmosis membrane layer, the second porous permeate layer, the third reverse osmosis membrane layer, the first porous permeate layer, the second reverse osmosis membrane layer, the porous mesh layer and the first reverse osmosis membrane layer.

The nonporous semi-permeable membrane layers of the first and the second reverse osmosis membrane layers are disposed adjacent the porous mesh layer. Preferably, the nonporous semi-permeable membrane layers of the third and the fourth reverse osmosis membrane layers are disposed adjacent the second porous permeate layer.

In an alternative embodiment for purifying water from a source, the method comprises passing water from the source through a first reverse osmosis means being in fluid communication with the source so as to purify at least a first portion of the water from the source; passing the purified first portion of water through chemical means being in fluid communication with the first reverse osmosis means to receive the first purified portion of water and for removal of at least chemical contaminants from the first purified portion of water; and passing the chemically purified water through a second reverse osmosis means being in fluid communication with the chemical means to receive the chemically purified water for purification of at least a second portion of the chemically purified water, the second reverse osmosis means also being in fluid communication with the first outlet and the second outlet so as to permit passage of the second portion of purified water through the first outlet and for passage of waste water through the second outlet.

In yet another preferred embodiment, after passing water from the source through a first reverse osmosis means so as to purify at least a first portion of the water from the source, the method comprises passing the purified first portion of water through a second reverse osmosis means being in fluid communication with the first reverse osmosis means to receive the purified first portion of water for further purification of at least a second portion of the water; and passing the purified second portion of water through chemical means being in fluid communication with the second reverse osmosis means to receive the second purified portion of water and for removal of at least chemical contaminants from the purified second portion of water, the chemical means also being in fluid communication with the first outlet so as to permit-passage of the chemically purified water through the first outlet. If desired, the purified water can be passed through a filtration means for further purification.

The present invention also is directed to a peritoneal dialysis system for treating a patient comprising reverse osmosis device for purifying water from a source and having input means for coupling to the source of water; first reverse osmosis means being in fluid communication with the input means for purification of at least a first portion of the water from the source; and second reverse osmosis means being in fluid communication with the first reverse osmosis means to receive the purified first portion of water for further purification of at least a second portion of the water; means for supplying a predetermined amount of drug and means for mixing the purified second portion of the fluid with the concentrate to provide a dialysate solution; and means for delivering the dialysate solution to the peritoneal cavity of the patient.

The system further comprises means for draining waste water from the reverse osmosis device and also means for draining spent dialysate solution from the peritoneal cavity of the patient.

The delivering means can be adapted to include, but not be limited to, continuous, intermittent, tidal or continuous ambulatory peritoneal dialysis treatment of the patient as well as other treatments including hemodialysis.

The system further comprises means for heating the water from the source. The water can be heated up to about 70° C., preferably up to about 50° C., for example up to 36° C., to increase the efficiency of the reverse osmosis device. The heating means is coupled to the input means of the reverse osmosis device so as to heat the water before purification. A high pressure pump can be fluidly coupled between the heater means and the reverse osmosis device so as to provide sufficient pressure to allow for proper operation of the reverse osmosis device. The reverse osmosis device further includes a first outlet for passage of purified water from the second reverse osmosis means and a second outlet for passage of waste water remaining after purification. The reverse osmosis device can further comprise a third outlet in fluid communication with the first reverse osmosis means so as to permit passage of waste water through the third outlet.

Also, a heat exchanger means can be fluidly coupled to the second outlet of the reverse osmosis device and can be disposed in thermal relationship with the water from the source so as to provide for transfer of heat from the waste water to the water to be heated. Also heat exchanger means can be fluidly coupled to the means for draining spent. dialysate solution and disposed in thermal relationship with the water from the source so as to provide for transfer of heat from the solution to the water to be heated. The supplying means comprises a storage bag having a coupling end and containing a predetermined drug and a metering system such as a syringe, or a precision pump in fluid communication with the coupling end of the storage container to receive a predetermined amount of drug and also is in fluid communication with the purified second portion of the water after passing through the first outlet.

The system further comprises means for sterilizing the coupling end of the storage container when being coupled and decoupled to the metering system.

The mixing means is in fluid communication with the first outlet and the metering means so as to receive the purified second portion of the water and the predetermined amount of drug for preparation of a dialysate solution. The mixing means can be any of an ultrasonic, electromechanical, electromagnetic or static mixer.

In one alternative embodiment, the delivery means comprises a dual lumen catheter affixed to the patient and adapted for fluid communication at one end of one lumen with the peritoneal cavity of the patient and at the other end of the one lumen with the mixing means so as to allow for delivery of the dialysate solution to the peritoneal cavity. The other lumen is adapted for fluid communication with the peritoneal cavity of the patient at one end and at the other end with a drain means to receive the spent dialysate solution from the peritoneal cavity.

In another embodiment, the delivery means comprises a single lumen catheter affixed to the patient and adapted for fluid communication at one end of the lumen with the peritoneal cavity of the patient and at the other end of the lumen with the mixing means so as to allow for delivery of the dialysate solution to the peritoneal cavity. A pump can be fluidly coupled, as desired, between the supplying means and the reverse osmosis device, between the mixing means and the peritoneal cavity of the patient, and between the peritoneal cavity of the patient and an isolation valve and a drain means for receiving the used dialysate solution. Also, a computer can be employed for predetermined, selective and automatic control of the delivery means. The system can further comprise chemical means positioned in fluid communication with the second reverse osmosis means to receive said second purified portion of water and for removal of at least chemical contaminants from the second purified portion of water.

A method for treating a patient comprises purifying water from a source with a reverse osmosis device having input means for coupling to the source of water; first reverse osmosis means being in fluid communication with the input means for purification of at least a first portion of the water from the source; and second reverse osmosis means being in fluid communication with the first reverse osmosis means to receive the purified first portion of water for further purification of at least a second portion of the water; supplying a predetermined amount of drug; mixing the drug with the purified second portion of the water so as to provide a dialysate solution; and delivering the dialysate solution to the peritoneal cavity of the patient. The delivery of the dialysate solution can be continuous, intermittent, of the tidal mode of treatment or of the continuous ambulatory mode of treatment. Preferably, the water is heated and is pumped under a predetermined pressure prior to purification.

Also, at least a portion of the waste water from the reverse osmosis device can be returned to a heat exchanger means disposed in thermal relationship with the water from the source so as to provide for transfer of heat from the waste water to the water to be heated. At least a portion of the spent dialysate solution can be returned to a heat exchanger means disposed in thermal relationship with the water from the source so as to provide for transfer of heat from the dialysate solution to the water to be heated. Moreover, the first purified portion of water can be passed through chemical means being in fluid communication with the first reverse osmosis means for removal of at least chemical contaminants from the first purified portion of water before passing on to the second reverse osmosis means. Alternatively, the second purified portion of water can be passed through chemical means being in fluid communication with the second reverse osmosis means for removal of at least chemical contaminants from the second purified portion of water. Also the chemically treated water portion can be passed through a filtration means fluidly coupled to the chemical means for further purification of the water portion. The method further comprises draining waste water from the reverse osmosis device. Also the method can further comprise draining spent dialysate solution from the peritoneal cavity of the patient. Another system for supplying purified water from a source comprises a reverse osmosis device according to the present invention and means for delivering the purified second portion of the water to either a storage means for future use or to a control means for immediate predetermined use.

The present invention is moreover directed to a hemodialysis system for treating a patient comprising reverse osmosis device for purifying water from a source and having input means for coupling to the source of water; first reverse osmosis means being in fluid communication with the input means for purification of at least a first portion of the water from the source; and second reverse osmosis means being in fluid communication with the first reverse osmosis means to receive the purified first portion of water for further purification of at least a second portion of the water; and means for supplying a predetermined amount of drug; means for mixing the purified second portion of the water with the drug to provide a dialysate solution; and means for delivering the dialysate solution to a hemodialyzer. The system further comprises means for draining waste water from the reverse osmosis device and also means for draining spent dialysate solution from the hemodialyzer. The reverse osmosis device further comprises chemical means being in fluid communication with the first reverse osmosis means to receive the first purified portion of water and for removal of at least chemical contaminants from the first purified portion of water before passing on to the second reverse osmosis means. Means for heating the water from the source is provided and is coupled to the input means of the reverse osmosis device so as to heat the water before purification. A high pressure pump is fluidly coupled between the source and the reverse osmosis device so as to provide sufficient pressure to allow for proper operation of the reverse osmosis device. The system further comprises means for heating the water from the source which is fluidly coupled between the high pressure pump and the source so as to heat the water before purification. The means for heating the water from the source can also be fluidly coupled between the high pressure pump and the reverse osmosis device so as to heat the water before purification. The reverse osmosis device further includes a first outlet for passage of purified water from the second reverse osmosis means and a second outlet for passage of waste water. The reverse osmosis device further comprises a third outlet for passage of waste water. The apparatus first osmosis means is in fluid communication with the third outlet so as to permit passage of waste water through the third outlet. The second reverse osmosis means is in fluid communication with the second outlet for passage of waste water through the second outlet. A heat exchanger means is fluidly coupled to the second and/or third outlet of the reverse osmosis device and is disposed in thermal relationship with the water from the source so as to provide for transfer of heat from the waste water to the water to be heated. Alternatively, the heat exchanger means can be fluidly coupled to the means for draining spent dialysate solution and disposed in thermal relationship with the water from the source so as to provide for transfer of heat from the solution to the water to be heated.

According to the system, the supplying means comprises a storage container having a coupling end and containing a predetermined drug, and a metering system in fluid communication with the coupling end of the storage container to receive a predetermined amount of drug and is further in fluid communication with the purified second portion of the water after passing through the first outlet. The system further comprises means for sterilizing the coupling end of the storage container when being coupled and decoupled to the metering system. The mixing means is in fluid communication with the first outlet and the metering system so as to receive the purified second portion of the water and the predetermined amount of drug for preparation of a dialysate solution. The mixing means can be an ultrasonic, electromagnetic, electromechanical or a static mixer. Pump means is fluidly coupled between the supplying means and the reverse osmosis device. Pump means can also be fluidly coupled between the mixing means and the hemodialyzer, and also between the hemodialyzer and a drain means for receiving the spent dialysate solution. A computer means provides for predetermined, selective and automatic control of the delivery means, the supplying means, the mixing means and the draining means.

The present invention is also directed to a system for irrigating a portion of a patient's body comprising a reverse osmosis device according to the present invention and means for supplying the purified second portion of the water to the portion of the patient's body. The system can further comprise means for supplying a predetermined amount of drug; means for mixing the purified second portion of the water with the drug to provide a drug solution; and means for delivering the drug solution to the portion of the patient's body. The supplying means is adapted for irrigating a wound or a cavity of a patient with the drug mixture. The supplying means can also include a humidifying means which is adapted for humidification of a patient's lungs.

In addition, the present invention is directed to a system for delivery of a predetermined injectable drug to a patient comprising a reverse osmosis device according to the present invention; means for supplying and mixing the predetermined drug with the purified second portion of water; and means for supplying the said drug and purified water mixture to a body portion of the patient.

A heat exchanger according to the present invention for transferring heat to a first source of fluid from a second source of fluid comprises an elongated core; first film composite having a first porous mesh and a first fluidly impermeable layer; second film composite having a second porous mesh and a second fluidly impermeable layer; the first and the second film composites being disposed in an interleaf configuration and being disposed about the core so as to provide a first fluid flow path generally between the core and the first fluidly impermeable layer and a second fluid flow path between the first fluidly impermeable layer and the second fluidly impermeable layer such that heat from fluid in one of the first and the second flow paths can be transferred to the fluid in the other flow path.

The core is generally cylindrical and the first and the second film composites are generally rectangular and are spirally rolled about the core. The first and the second fluidly impermeable layers are each formed of a metallic foil, an impermeable polymeric film, or an impermeable inorganic film. The heat exchanger further comprises means for fluidly sealing the first and the second film composites along one edge to the core and also sealing to the core the adjacent edges transverse to the one edge. Preferably the sealing means comprises an impermeable adhesive. The heat exchanger further comprises an elongated hollow cylindrical housing container having a base and an open end. The housing container includes a cap configured and dimensioned to fluidly seal the open end and includes an inlet passageway for admitting fluid from the first source, a first outlet for passage of the first source after heating, a second inlet for passage of said second source and a second outlet for passage of the second source after transfer of heat to the first source.

In one embodiment, the first inlet and the first outlet are in fluid communication with the first fluid path, and the second inlet and second outlet are in fluid communication with the second fluid path.

A peritoneal dialysis system according to the present invention for treating a patient comprises a reverse osmosis device for purifying water according to the present invention wherein the reverse osmosis device is formed of radiation sterilizable components; means for supplying a predetermined amount of drug; means for mixing the purified second portion of the water with the drug to provide a dialysate solution; and means for delivering the dialysate solution to the peritoneal cavity of the patient. The supplying means is selectively replaceable in the system and is adapted for maintaining sterile fluid couplings and decouplings in the system. Similarly, the mixing means and delivering means are adapted for maintaining sterile fluid couplings and decouplings in the system. The system further comprises means for draining spent dialysate solution from the peritoneal cavity of the patient. The draining means includes a one way isolation valve to prevent any retrograde biocontamination of the peritoneal cavity of the patient.

In one embodiment, the supplying means comprises a storage container having a coupling end and containing a predetermined drug, and a metering system in fluid communication with the coupling end of the storage container to receive a predetermined amount of drug and further is in fluid communication with the purified second portion of the water after passing through the first outlet. The system further comprises means for sterilizing the coupling end of the storage container when coupled and decoupled to the metering system. Preferably, the mixing means is in fluid communication with the first outlet and the metering system so as to receive the purified second portion of the water and the predetermined amount of drug for preparation of a dialysate solution. The system further comprises first pump means fluidly coupled between the mixing means and the reverse osmosis device, second pump means fluidly coupled between the mixing means and the supplying means, third pump means adapted to be fluidly coupled between the mixing means and the peritoneal cavity of the patient and fourth pump means adapted for fluid coupling between the peritoneal cavity of the patient and a drain means for receiving the used dialysate solution. The first, second, third and fourth pump means comprise volumetric pumps which are calibratable. A second supplying means is adapted for fluid coupling to the peritoneal cavity of the patient for selective admission of a second predetermined drug. A fifth pump means is adapted for fluid coupling between the second supplying means and the peritoneal cavity of the patient. Also, the fifth pump means comprises a volumetric calibratable pump.

The system further comprises clamp means for selective and independent operation of the components of the system. The clamp means comprises a plurality of on-off clamps disposed at predetermined fluid positions of the system. A computer means is coupled to the plurality of on-off claims for automatic predetermined operation thereof.

The housing of the reverse osmosis device includes an elongated hollow first cylindrical container having a base and an open end. A generally cylindrical core is disposed within the housing and extends from the base to the cap. The first and second reverse osmosis means are rolled about the outer surface of the cylindrical core so as to provide for spiral flow paths of the water to be processed. The cylindrical core has a hollow central portion for receiving chemical means within the hollow central portion. The system further comprises a second cylindrical hollow container having a base and an open end and which is configured and dimensioned so as to be adapted to be positioned within the first container, and to receive and to seal the first reverse osmosis means therein. The housing includes a cap configured and dimensioned to fluidly seal the open end and includes an inlet passageway for admitting water from the source, a first outlet passageway for purified water and a second outlet passageway for waste water. The cap has an inner face and an outer face and further comprises a plurality of protrusions extending from the inner face into selective contacting relationship with the core at predetermined positions. The protrusions are fusable with the core upon application of at least one of ultrasonic and thermal energy. Also, the second cylindrical container has an inner face and further comprises a plurality of protrusions extending from the inner face into selective contacting relationship with the core at predetermined positions. The core has a plurality of passageways predeterminately coupled through the inner face of the cap and the inner face of the second container to provide fluid flow paths for the water from the source, the waste water and the purified water into, through and out of the housing.

The system comprises at least a first conductivity sensor disposed downstream of said source of purified water for monitoring of the conductivity of said water. A second conductivity sensor is disposed downstream of the mixing means for monitoring of the conductivity of the dialysate solution.

The system further comprises means for restricting the flow of water therethrough and also thereby through the reverse osmosis device. The flow restricting means comprises a flow plug configured and dimensioned so as to be adapted to be disposed within at least one passageway in the core. The flow plug has a reduced effective cross sectional area than the at least one passageway so as to restrict the flow of water through the passageway and provide for predetermined pressures on either side of the flow plug. Preferably, at least two flow plugs are disposed in a different passageway in the core. A computer means is coupled to the first and the second conductivity sensors for selective, predetermined operation of the system.

A method of manufacturing a reverse osmosis device on a core for purifying water from a source comprises providing an integral reverse osmosis multilayer assembly having first reverse osmosis membrane layer; porous mesh layer; second reverse osmosis membrane layer; and porous permeate layer; sealing a central portion of the integral multilayer assembly; sealing at least one edge of the multilayer assembly to the core; sealing along two opposed side edges of the integral multilayer assembly; rolling the integral multilayer assembly in a spiral configuration on the core; and bonding the seals by induction heating so as to fluidly seal the integral multilayer assembly along the edges and the central portion and so as to separate the integral multilayer assembly into a first reverse osmosis multilayer assembly and a second reverse osmosis multilayer assembly. In one embodiment, sealing is obtained by disposing an impermeable adhesive along the length of a central portion of the integral multilayer assembly; and disposing an impermeable adhesive along the side edges of the integral multilayer assembly.

The method further comprises enclosing the spirally rolled and bonded integral multilayer assembly in a housing having an inlet for passage of water for a source, a first outlet for passage of purified water from the passage of purified water from the housing and a second outlet for passage of waste water remaining after purification, disposing the first reverse osmosis multilayer assembly within the housing in fluid communication with the inlet for purification of at least a first portion of the water from the source, and disposing the second reverse osmosis multilayer assembly within the housing in fluid communication with the first reverse osmosis means to receive the first purified portion of water for purification of at least a second portion of the purified water, the second reverse osmosis means also being disposed in fluid communication with the second outlet for passage of waste water through the second outlet.

Alternatively, the method can comprise providing an integral reverse osmosis multilayer assembly having first reverse osmosis membrane layer; first porous mesh layer; second reverse osmosis membrane layer; porous permeate layer; third reverse osmosis membrane layer; second porous permeate layer; fourth reverse osmosis membrane layer; and third porous permeate layer.

The present invention is also directed to a device for sterile coupling and decoupling of a drug container to a delivery system, the container having an open end and a puncturable seal adapted for entry into the open end so as to seal the open end comprising a housing configured and dimensioned for receiving and cooperating with the plug so as to provide a fluid tight cooperating engagement when the plug enters the housing; barrier means disposed within the housing and having a portion thereof adapted for sterile penetration of the barrier means by a conduit of the delivery system; an inlet duct and an outlet duct disposed through the housing and disposed between the barrier means and the plug when positioned within the housing. The inlet duct is adapted for fluid coupling to a source of sterilizing fluid, and the outlet duct is adapted for fluid coupling to a reservoir container to receive the sterilizing fluid after passing across the portion of the plug facing the barrier means.

The present invention is also directed to a hemoultrafiltration system for treating a patient comprising reverse osmosis device for purifying water from a source and having input means for coupling to the source of water; first reverse osmosis means being in fluid communication with the input means for purification of at least a first portion of the water from the source; and second reverse osmosis means being in fluid communication with the first reverse osmosis means to receive the purified first portion of water for -further purification of at least a second portion of the water; and means for supplying a predetermined amount of drug; means for mixing the purified second portion of the water with the drug to provide a blood make up solution; and means for delivering the blood make up solution to the concentrated blood outlet of a hemoultrafilter. The system further comprises means for draining waste water from the reverse osmosis device and also means for draining spent waste solution from the hemoultrafilter. The reverse osmosis device further comprises chemical means being in fluid communication with the first reverse osmosis means to receive the first purified portion of water and for removal of at least chemical contaminants from the first purified portion of water before passing on to the second reverse osmosis means. Means for heating the water from the source is provided and is coupled to the input means of the reverse osmosis device so as to heat the water before purification. A high pressure pump is fluidly coupled between the source and the reverse osmosis device so as to provide sufficient pressure to allow for proper operation of the reverse osmosis device. The system further comprises means for heating the water from the source which is fluidly coupled between the high pressure pump and the source so as to heat the water before purification. The means for heating the water from the source can also be fluidly coupled between the high pressure pump and the reverse osmosis device so as to heat the water before purification. The reverse osmosis device further includes a first outlet for passage of purified water from the second reverse osmosis means and a second outlet for passage of waste water. The reverse osmosis device further comprises a third outlet for passage of waste water. The apparatus first osmosis means is in fluid communication with the third outlet so as to permit passage of waste water through the third outlet. The second reverse osmosis means is in fluid communication with the second outlet for passage of waste water through the second outlet. A heat exchanger means is fluidly coupled to the second and/or third outlet of the reverse osmosis device and is disposed in the final relationship with the water from the source so as to provide for transfer of heat from the waste water to the water to be heated. Alternatively, the heat exchanger means can be fluidly coupled to the means for draining spent waste solution and disposed in thermal relationship with the water from the source so as to provide for transfer of heat from the solution to the water to be heated.

According to the system, the supplying means comprises a storage container having a coupling end and containing a predetermined drug, and a metering system in fluid communication with the coupling end of the storage container to receive a predetermined amount of drug and is further in fluid communication with the purified second portion of the water after passing through the first outlet. The system further comprises means for sterilizing the coupling end of the storage container when being coupled and decoupled to the metering system. The mixing means is in fluid communication with the first outlet and the metering system so as to receive the purified second portion of the water and the predetermined amount of drug for preparation of a blood make up solution. The mixing means can be an ultrasonic, electromagnetic, electromechanical or a static mixer. Pump means is fluidly coupled between the supplying means and the reverse osmosis device. Pump means can also be fluidly coupled between the mixing means and the hemofilter, and also between the hemofilter and a drain means for receiving the spent waste solution. A computer means provides for predetermined, selective and automatic control of the delivery means, the supplying means, the mixing means and the draining means.

BRIEF DESCRIPTION OF THE DRAWINGS

The present invention is described in greater detail hereinbelow, with reference to the drawings wherein:

FIG. 12B is an inside view of the second pressurized container inside the housing of the RO device according to the present invention.

FIG. 20 is a cross sectional view of yet another alternative embodiment of an RO device according to the present invention wherein the inlet port is at a different end than the outlet ports.

FIG. 25 is a side end view of the first and second layers of the heat exchanger prior to assembly about the core.

FIG. 26 is top view of the second layer of FIG. 25 with the first layer removed.

FIG. 28 is a side view of a restrictor for use in the RO device according to the present invention.

FIG. 28A is a view along lines 28A-28A of FIG. 28.

FIG. 29 is a perspective view of the restrictor of FIG. 27.

DESCRIPTION OF THE PREFERRED EMBODIMENTS

In the description which follows, any reference to either orientation or direction is intended primarily for the purpose of illustration and is not intended in any way as a limitation of the scope of the present invention.

Figure 1:
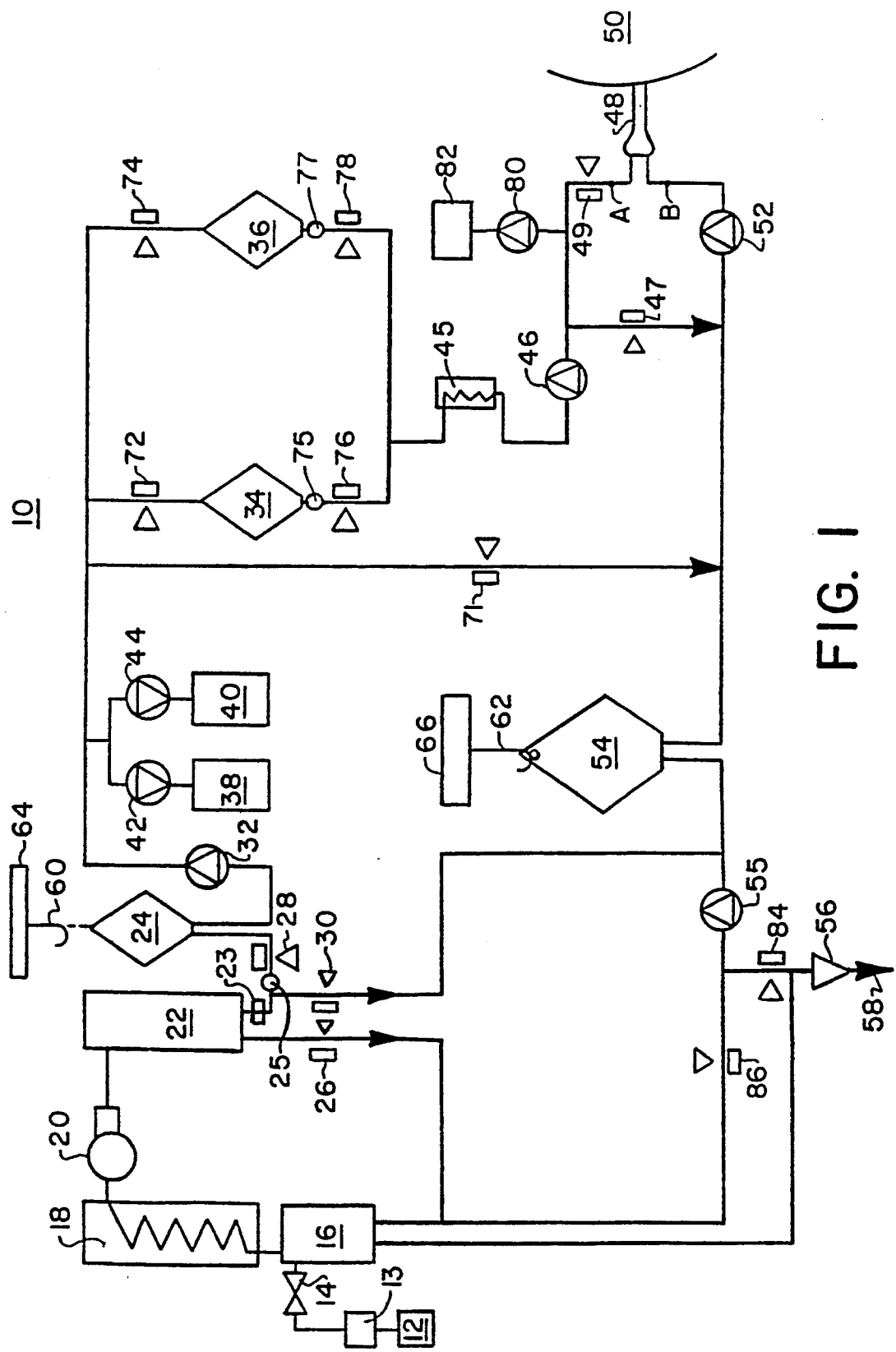
FIG. 1 is a schematic view of an automatic peritoneal dialysis system employing an RO device according to the present invention.

The peritoneal dialysis system (PDS) 10 of FIG. 1 of the present invention is designed to preferably utilize potable water and prepackaged drug mixtures or concentrate to enable a patient to obtain peritoneal dialysis at home and preferably at night. If desired, other sources of water can be utilized as well. For instance, non-potable tap water can be used to produce potable water by the RO device which in turn can be utilized by the peritoneal dialysis system.

As shown in FIG. 1, water from a source 12 is admitted optionally through prefilter 13 to remove particulates which are greater or equal to about 5 microns in size and through a valve 14 and heat exchanger 16 into a heater 18 and thereafter is passed through a high pressure pump 20 to the reverse osmosis (RO) device 22 according to the present invention. Within the RO device 22, some of the potable water is purified and exits optionally through a sterilizing filter 23 into a surge container such as a bag 24. The waste water is passed through an on/off clamp 26 to the heat exchanger 16. The heat exchanger 16 transfers at least a portion of the heat from the waste water so as to warm the original potable water before the potable water passes through heater 18. The on/off clamp 28 can regulate the passage of the purified permeate to the surge container 24 and an on/off clamp 30 can alternatively allow for passage of excess permeate to the drain or another collection container for storage through the isolation one-way valve 56.

A conductivity sensor 25 is placed downstream of the RO device 22 to continually or periodically monitor the electrical resistivity of the purified permeate water. Alternatively, the conductivity sensor may be placed downstream of on/off clamp 30 to periodically monitor the electrical resistivity of the purified permeate.

A pump 32 passes the ultrapure water or permeate from the surge container 24 to mixing bags 34 and 36. Concentrate such as a prepared drug or other desired mixture from sources 38 and 40 passes through metering pumps 42 and 44 that pass a predetermined amount of concentrate into the mixing container 34 and 36 that can mix and measure and alternatively feed to the downstream pump 46. Also, drug sources in addition to sources 38, 40 can be provided, as desired, or only one may be utilized if preferred. In a preferred embodiment, source 38 could include a predetermined dextrose solution of about 65% concentrate. To allow for conductivity monitoring, the dextrose source 38 can be provided with a predetermined amount of electrolytes that can be measured upon coming into contact with conductivity sensor, which will be discussed in more detail below. Similarly, other sources can be provided with electrolyte markers that would allow for conductivity measurement as well. Of course, to the extent that other sources already contain electrolytes, any additional markers are not required but could aid in the measurement process. Conductivity sensors 75 and 77 are placed downstream of mixing bags 34 and 36 respectively so as to continually or periodically monitor the electrical resistivity of the mixed solutions from the mixing bags. Alternatively a conductivity sensor may be placed downstream of clamp 76 and 78 so as to periodically monitor the electrical resistivity of the mixed solutions from the mixing bags. The conductivity sensors may also be used to aid in the formulation of the dialysate.

Advantageously, a heater 45 is used to control the temperature of the dialysate within desired ranges.

By means of the high accuracy pump 46, the dialysate is then admitted through a dual lumen catheter 48 into a patient's peritoneal cavity 50. Discharge from the patient is provided by a downstream high accuracy pump 52 into a discharge measurement container 54 and thereafter, through pump 55 and an isolation one-way valve 56, which serves as a barrier against virus, bacteria and pyrogen, to a drain 58. Alternatively, with the on/off clamp 84 closed and on/off clamp 86 opened, the discharge from the patient passes through the heat exchanger 16 to transfer at least a portion of the heat from the discharge so as to warm the original potable water before the potable water passes through heater 18. The discharge is subsequently drained off through isolation one-way valve 56 to drain 58.

The surge container 24 is optionally supported by hook means 60 which is connected to weight measurement mechanism 64. The discharge measurement container 54 is supported by hook means 62 which is connected to weight measurement mechanism 66. In one preferred embodiment, the weight measurement mechanisms provide electrical signals corresponding to the weight of the contents of the respective container. These signals are transmitted to a computer control system (not shown in FIG. 1) that is discussed in greater detail below.

As shown in FIG. 1, an outlet through on/off clamp 71 is provided upstream of the mixing containers 34 and 36 for flushing, priming and calibrating. Additional clamps 72 and 74 are provided to close off the downstream flow paths when clamp 71 is opened. In this manner, the permeate or ultrapure water combining with concentrate from sources 38 and 40 can initially be passed through isolation valve 56 to drain until proper operation and priming is obtained. Thereafter, clamp 71 is closed and clamps 72 and/or 74 are opened according to the desired operation. When clamps 72 and 74 are closed and clamp 71 is left open, the discharge measurement container 54 along with the hook means 62 and weight measurement mechanism 66 can then be used to calibrate the delivery rate of the pumps 32, 42 and 44 individually. Similarly, when clamp 47 is opened and clamp 49 is closed, the discharge measurement container 54 along with the hook means 62 and weight measurement mechanism 66 can be used to calibrate pumps 46 and 80 individually. When both clamps 47 and 49 are closed, calibration of pump 52 can be performed. Other on/off clamps 76 and 78 control the outflow from mixing containers 34 and 36.

The on/off clamp 86 and pump 55 control the flow of the discharge from the discharge measurement container 54 to the heat exchange 16 and isolation one-way valve 56. Alternatively, with clamp 86 closed, the discharge can flow through pump 55 and clamp 84 to the isolation one-way valve 56 to drain 58.

Within the mixing containers 34 and 36, the concentrate and permeate are adequately mixed to provide a dialysate solution suitable for the peritoneal dialysis treatment of the patient 50. The mixing can be performed by known methods which include, for example, ultrasonic, mechanical, static and also electromechanical modes of mixing. One preferred embodiment of mixing apparatus is of the electromechanical type and is described in greater detail below.

Optionally, a container 82 and pump 80 are connected just upstream of clamp 49 to provide a method of administering drugs into the patient 50. Such drugs include but are not limited to insulin, heparin, antibiotics, erythro poietin, and nutritional supplements like calcium, magnesium and amino acids.

The dual lumen catheter 48 is of a configuration that is surgically implanted into the patient 50 and extends into the peritoneal cavity by appropriate lumen tubing (not shown) as is well known to those in the medical art. One lumen is coupled to the pump 46 while the other lumen is coupled to discharge pump 52.

Figure 3:
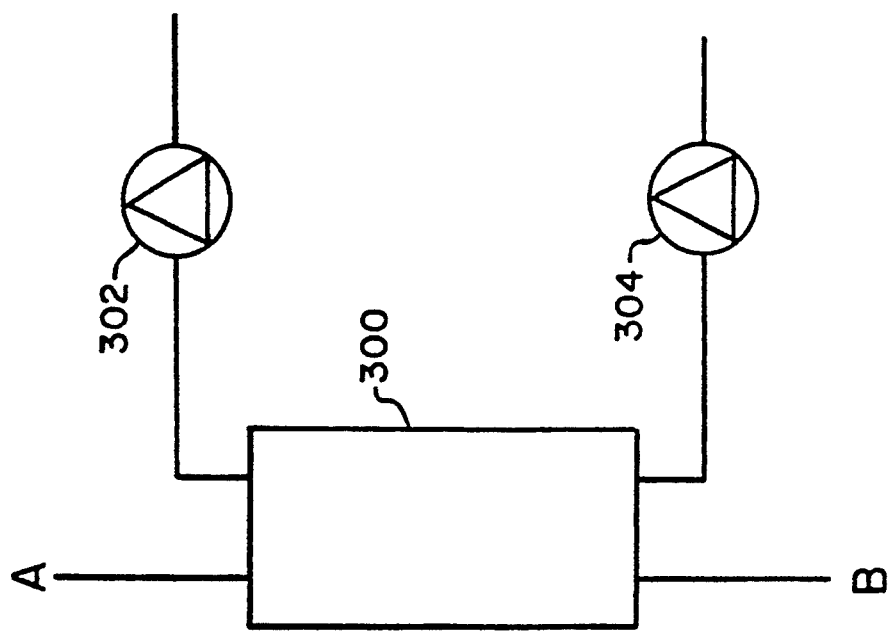
FIG. 3 is a partial schematic view of the system of FIG. 1 adapted for use with a hemodialyzer.
Figure 2:
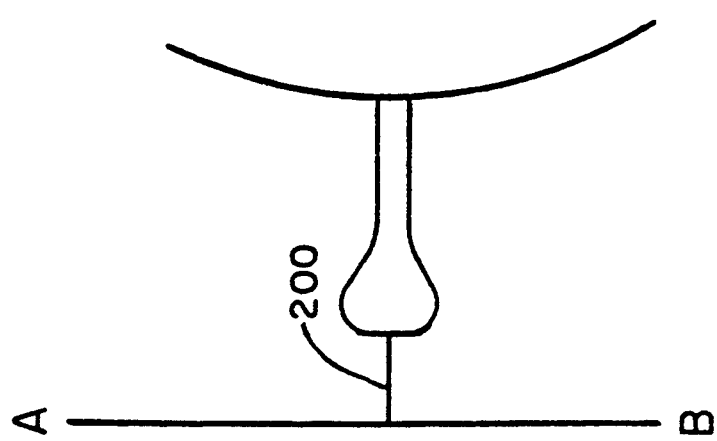
FIG. 2 is a partial schematic view of the automatic peritoneal dialysis system of FIG. 1 for use with a single lumen catheter.
Figure 36:
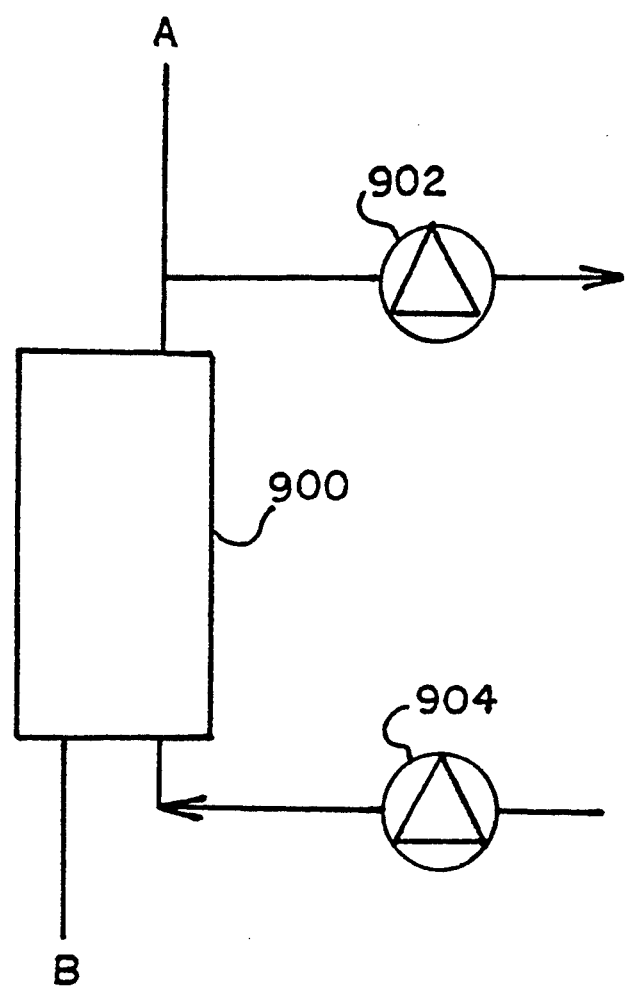
FIG. 36 is a partial schematic view of the system of FIG. 1 generally adapted for use in hemofiltration.

In operation, potable water such as from a tap, is passed through valve 14, warmed to the desired temperature by heat exchanger 16 and heater 18 and pumped under pressure through pump 20 into RO device 22. Some of the tap water is purified and sterilized so as to be free of pyrogens and to have an electrical resistivity of greater than approximately 0.05 megaohms per centimeter, which corresponds to about 25 ppm dissolved solids content, as determined by conductivity sensors. Waste water exits through clamp 26 and goes into the heat exchanger 16. The purified water or permeate is optionally passed through a sterilizing filter (i.e., .22 micrometer ($\mu$m) filter) and then admitted into a surge container 24 where it is optionally measured and stored, as desired, until pumped out by pump 32 into mixing containers 34 and/or 36. Also, concentrate of a prepared drug and treatment mixture, in paste, liquid or solid form is premeasured in source 38 and 40 and advanced by metering device such as pumps 42 and 44 or other delivery techniques or methodologies into the flow path passing with the permeate into the mixing containers 34 and/or 36. After suitable mixing the dialysate solution in mixing containers 34 and/or 6 is pumped into the patient 50 by pump 46 through one lumen of the dual lumen catheter 48. Optionally, drugs may be administered to the patient 50 by pumping the drugs from containers 82 into the line just upstream of the catheter. In a continuous mode of operation, the waste dialysate is pumped from the peritoneal cavity through pump 52 to the drain 58 or alternatively to heat exchanger 16 before being released through drain 58. The PDS system 10 of the present invention can also be operated for intermittent and tidal modes of peritoneal dialysis treatment, as desired. In some modes, the dual lumen catheter 40 can be replaced at points A and B with a single lumen catheter in accordance with known procedures as shown in FIG. 2.

Where the present system is adapted to supply sterile dialysate for use with a hemodialyzer 300, the catheter is replaced at points A and B by fluid connections to a hemodialyzer 300 as shown in FIG. 3. Metering pumps 302 and 304 are used to flow the patient's blood into and out of the hemodialyzer 300. Alternatively, the catheter can be replaced at points A and B by fluid connections to a hemoultrafilter 900 as shown in FIG. 36. Metering pumps 902 and 904 are used to flow the patient's blood into and out of the hemoultrafilter 900. A general description of hemofiltration of blood is presented in "Handbook of Dialysis", Little, Brown and Company, Boston/Toronto (1988) at pages 144-45 which are incorporated herein by reference. In the course of hemofiltration treatment, about 25 to 120 liters of blood make up solution will be supplied from point A in FIG. 36 to be combined with the concentrated blood exiting from the hemoultrafilter device 900. Waste solution exits from the hemoultrafilter device at point B.

Figure 35:
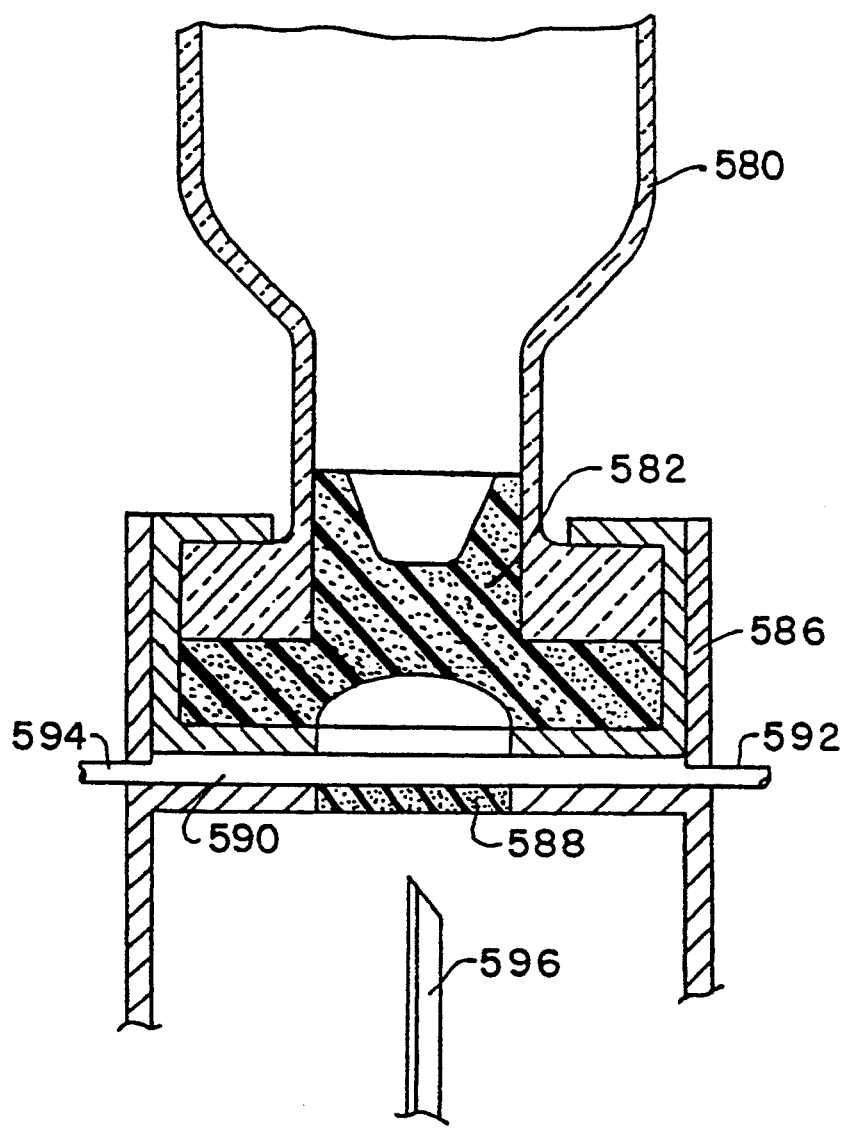
FIG. 35 is a method of performing a sterile connection.

The flow paths shown in FIG. 1 are provided by tubing well known to medical personnel. However, the tubing or flow paths downstream of the RO device 22 and through to the catheter 48 are maintained preferably in a sterile condition. For this reason, connections or couplings of the tubings and the various components of the PDS system 10 are kept sterile as well. Preferably, these flow paths including the RO device are provided in a modular compartment, as described in greater detail below, so that the patient need only replace the module compartment when necessary to replenish the RO device or the concentrate. The RO device itself is sterilized by radiation. Likewise, the concentrate is sterilized by terminal sterilization or by a sterile filling technique as taught, for example, in U.S. patent application Ser. No. 07/510,317, R. J. Kruger, et al. filed Apr. 17, 1990 for "Method for Sterilizing and Enclosure with Non-Condensing Hydrogen Peroxide-Containing Gas", which is incorporated herein by reference. Alternatively, a sterile connecting technique described in FIG. 35 may be used for connecting containers 38, 40 and 82 to the system as shown in FIG. 1. As shown in FIG. 35, a glass bottle container 580 having a rubber septum cap 582 is placed into a receiving holder 586 having a rubber septum seal 588. The receiving holder 586 holds the rubber septum 582 in a fluidly sealed manner and is disposed adjacent to the rubber septum seal 588 so as to leave a space 590. Hydrogen peroxide solution from about 2% to about 50% concentration is then introduced into the space 590 through inlet 592 to sterilize the space 590. When the sterilization is completed the hydrogen peroxide solution may discharge through outlet 594. Subsequent to the sterilization the dual lumen needle 596 or optionally two needles is moved upward puncturing the rubber septum seal 588 and the rubber septum 582 so as to sterilely connect the glass bottle container 580 to the system.

Sterile decoupling may be performed by retracting the dual lumen needle 596 below the rubber septum seal 588. The rubber septum 582 can then be decoupled from receiving holder 586 without contaminating dual lumen needle 596.

To further maintain sterile conditions, fluid is drained out of the system through an isolation, one-way valve 56 so as to prevent the introduction of virus, bacteria and pyrogen from the drain 58.

The above combination of procedures for maintaining sterile conditions lessens or greatly reduces the likelihood of pyrogens and bacteria and viruses entering the flow paths and thereby the peritoneal cavity of patient 50. As a result of the system being able to maintain highly-sterile conditions, a final 0.22 $\mu$m sterilizing filter immediately upstream of the catheter is not required before the dialysate is delivered to the patient.

The PDS system 10 of the present invention allows not only daytime or acute use but also for nighttime peritoneal dialysis treatment of patients. In this manner, patients can avoid the difficulties and discomfort that occurs with other peritoneal dialysis treatments requiring hospital or clinic visits. It is advantageous to utilize nighttime treatment in order to permit the patient to lead a more normal life during the waking hours. In addition, the method of treatment preferably to be employed with the PDS system of the present invention will require less dialysate to be stored within the peritoneal cavity during the dry period since there will be sufficient dialyzation by the continuous surge and flushing of the dialysate through and from the peritoneal cavity during the wet period.

In addition, the PDS system 10 is a gentler treatment system than that which is obtained with the more dramatic hemodialysis. In addition, the psychological factors inherent in hemodialysis treatment are avoided by the present system. Furthermore, the PDS system 10 is a simpler and less complicated system than is required with hemodialysis. The PDS system 10 thus allows a patient to avoid the dramatic environment facing such a patient in a hospital or clinic for either hemodialysis or conventional peritoneal dialysis treatments.

Also, by allowing the peritoneal membrane to be dry for a good portion of the day, problems otherwise present with other treatments can be avoided or minimized. Furthermore, the PDS system 10 by means of the compact and low cost RO device or cartridge which need only be replaced once every one to six, preferably three days, will help to reduce the cost of treatment within the range of a greater number of patients. Furthermore, the PDS system 10 will allow for shipment of small volume prepackaged drug concentrates in a paste, liquid or dry state which can then be combined with the ultrapure water prepared directly at the patient's home site by means of the RO device cartridge.

In an alternative embodiment of the PDS system 10, the operation will be computer controlled and will only require an on-off button so that entire treatment programs can be implemented from a computer system.

Furthermore, diagnostic sensors may be included in order to measure the urea and other metabolites so as to provide for a constant monitoring and desired treatment of the patient. Such a computer system will also permit the patient or care giver to modify the treatment stages and the volume of treatment fluid as desired. Also, such a computer system will allow the treatment process to be fine tuned to the specific medical needs of the patient. In general, the PDS system 10 provides a custom care treatment as well as an improved quality of life for the patient.

One specific manner in which the PDS system 10 may control peritoneal dialysis is to control the fluid flow rates through pumps 46 and 52. Typically, the total volume introduced into the peritoneum is less that the total volume drained out of the peritoneum. This volume difference is due to the ultrafiltrate or excess water generated in the body which is drawn into the peritoneum by osmotic pressure and which contributes to the total volume of water draining out. The PDS system 10 may thus set the flow through pump 52 at a greater rate than through pump 46 to compensate for this volume difference.

Another manner of controlling the peritoneal dialysis is to set the maximum fluid pressure in the inlet line near point A to 48 inches of water and to set the outlet line near point B to a maximum of minus 38 inches of water. This effectively prevents the pressure within the peritoneum from exceeding 30 inches of water. Preferably, the pressure within the peritoneum should be less than eight inches of water and most preferably less than 5.5 inches of water. These pressure maximums are chosen so as to minimize the adverse effect of fluid pressure within the peritoneum to cardiac output and vital capacity as disclosed in "Reduction of Vital Capacity Due to Increased Intra-Abdominal Pressure During Peritoneal Dialysis", by L. Gotloib, et al., P. D. Bulletin, Vol. 1, 63–64 (1981), which is incorporated herein by reference.

Figure 4:
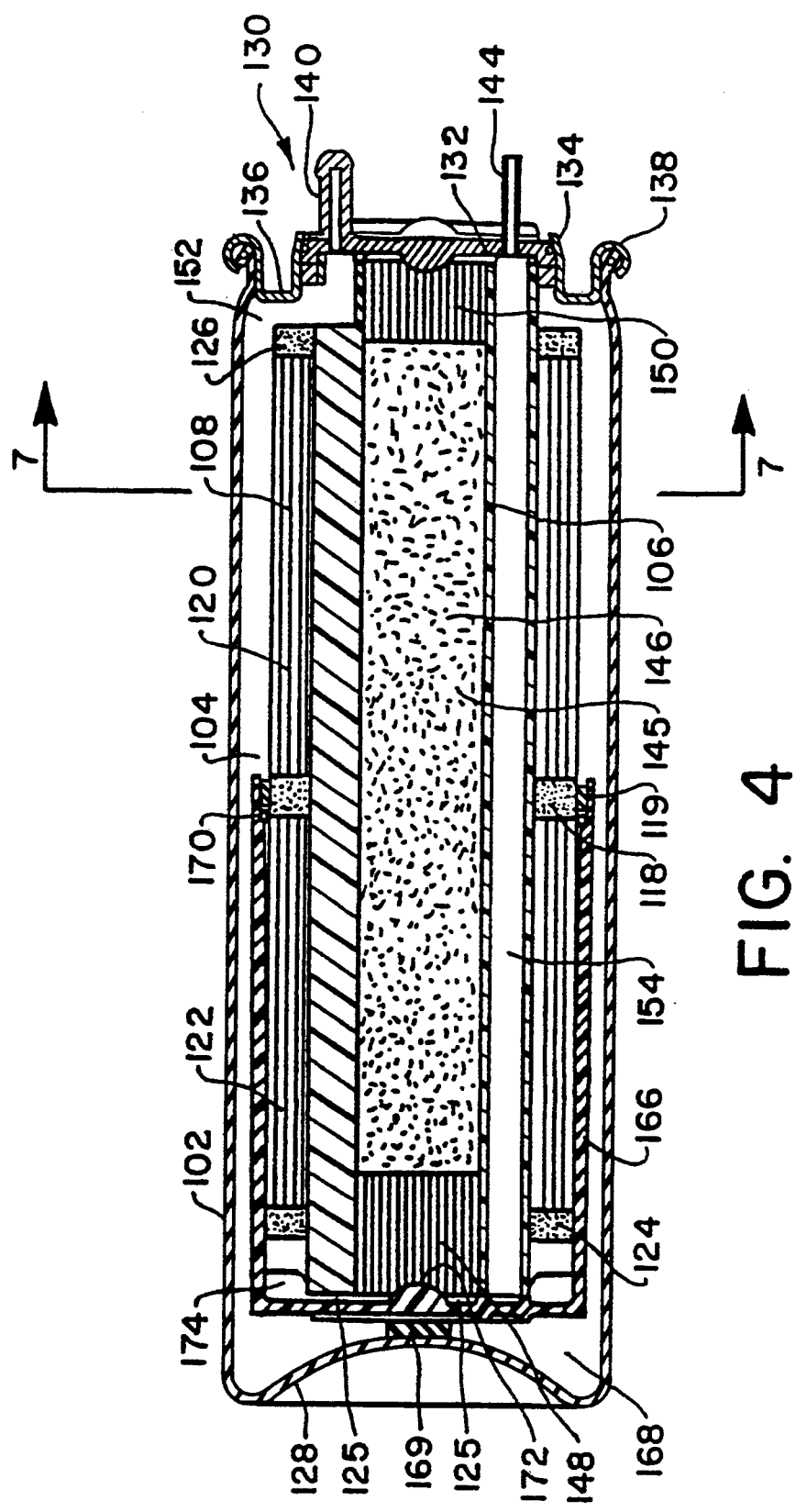
FIG. 4 is a cross sectional view of an RO device according to the present invention.
Figure 5:
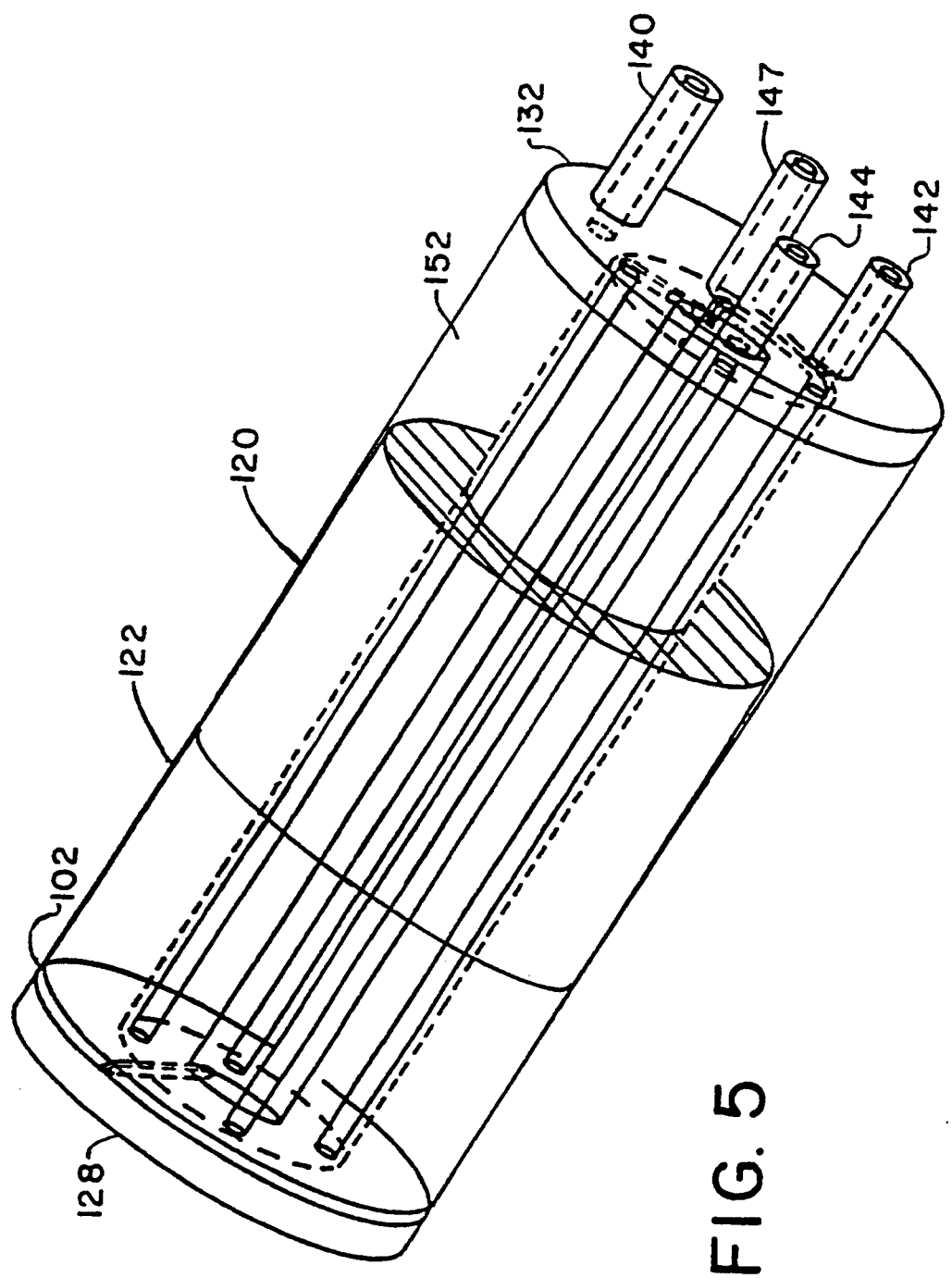
FIG. 5 is a perspective view exposed in part of the RO device of FIG. 4 to illustrate generally the internal components and arrangement.

As shown in FIGS. 4 and 5, the reverse osmosis (RO) cartridge of the present invention has a cylindrical hollow housing 102 forming a chamber 104 within which a hollow mandrel core 106 open at both ends is disposed within the chamber 104 so that the axis of the core 106 is coaxial to the axis of the chamber 104. The core preferably is formed of ABS plastic and can be molded but preferably extruded. The housing is formed of pressure-containing material—steel, fiberglas, Kevlar TM or aluminum to provide a light yet strong structure.

Figure 7:
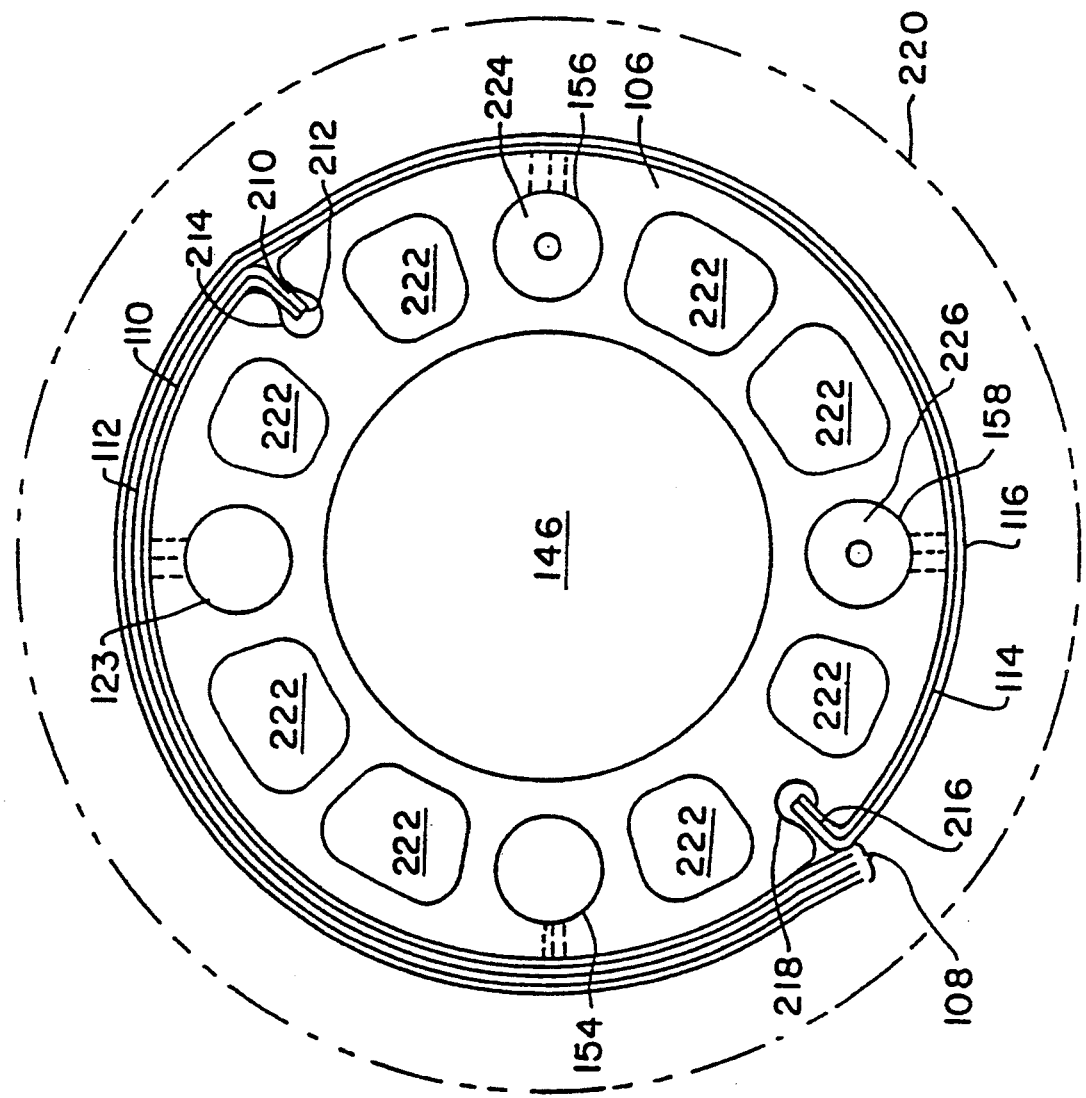
FIG. 7 is a cross sectional end view taken along the lines 7—7 of FIG. 4.
Figure 14:
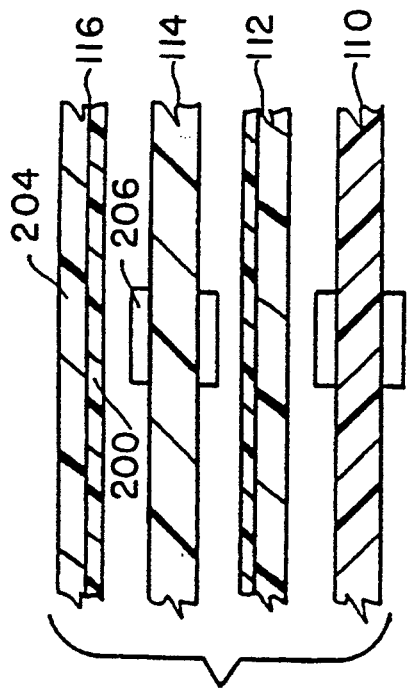
FIG. 14 is an exploded cross sectional view of the RO multilayer assembly of FIG. 13.
Figure 15:
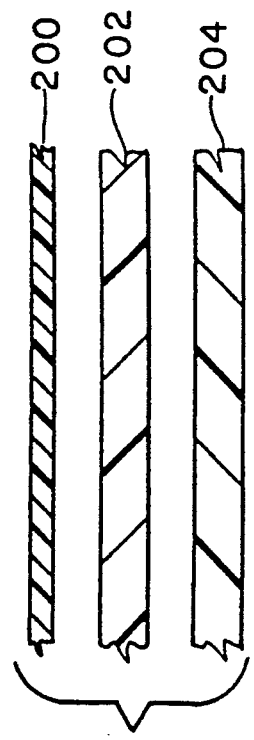
FIG. 15 is an exploded cross sectional view of the RO membranes of FIG. 14.

As shown in FIG. 14, an RO multilayer assembly 108 includes a porous permeate mesh or carrier layer 110, a first RO membrane layer 112, a feed water mesh or carrier layer 114 and second RO membrane layer 116. The RO membranes 112 and 116 are each formed of a composite, non-porous, semipermeable membrane 200, an ultrafiltration membrane 202 and a polyamide cloth 204 as shown in FIG. 15. RO membranes of this specific structure can be obtained from FilmTec Corporation, a division of Dow Chemicals, with a membrane designation of BW30. Such an RO membrane is also disclosed in U.S. Pat. No. 4,277,344 of J. E. Cadotte, assigned to FilmTec Corporation and issued Jul. 7, 1981 which is incorporated herein by reference. The RO multilayer assembly 108 is fixed to and rolled about the surface of the core 106 as shown in FIG. 7. An impermeable glue seal 118 is provided at about the middle of the RO multilayer assembly 108 prior to rolling and is disposed approximately perpendicular to the core 106 so that the glue seal 118 separates the RO multilayer assembly 108 into two stages 120 and 122 when the RO multilayer assembly 108 is spirally wound about the core 106. The side edges of the RO multilayer assembly 108 are also sealed by glue bonds 124 and 126. Thus the first and second stage 120, 122 are fluidly separated from one another. Preferably, the glue seal is made of a transparent glue capable of water vapor curing available under a trade name of H. B. Fuller Product #UR-0330. In order to provide visibility, the glue can be mixed with a coloring agent. Coloring agents include carbon black, fiber glass, mica, metallic particles, calcium carbonate and titanium dioxide at 0.25-3% by weight of glue preferably less than 1%. Particle size for the coloring agent range from 0.1 to 5 $\mu$m, preferably 1–2 $\mu$m. If carbon black is used, the glue becomes gray in color and also results in an improved wettability and better bonding.

Figure 9:
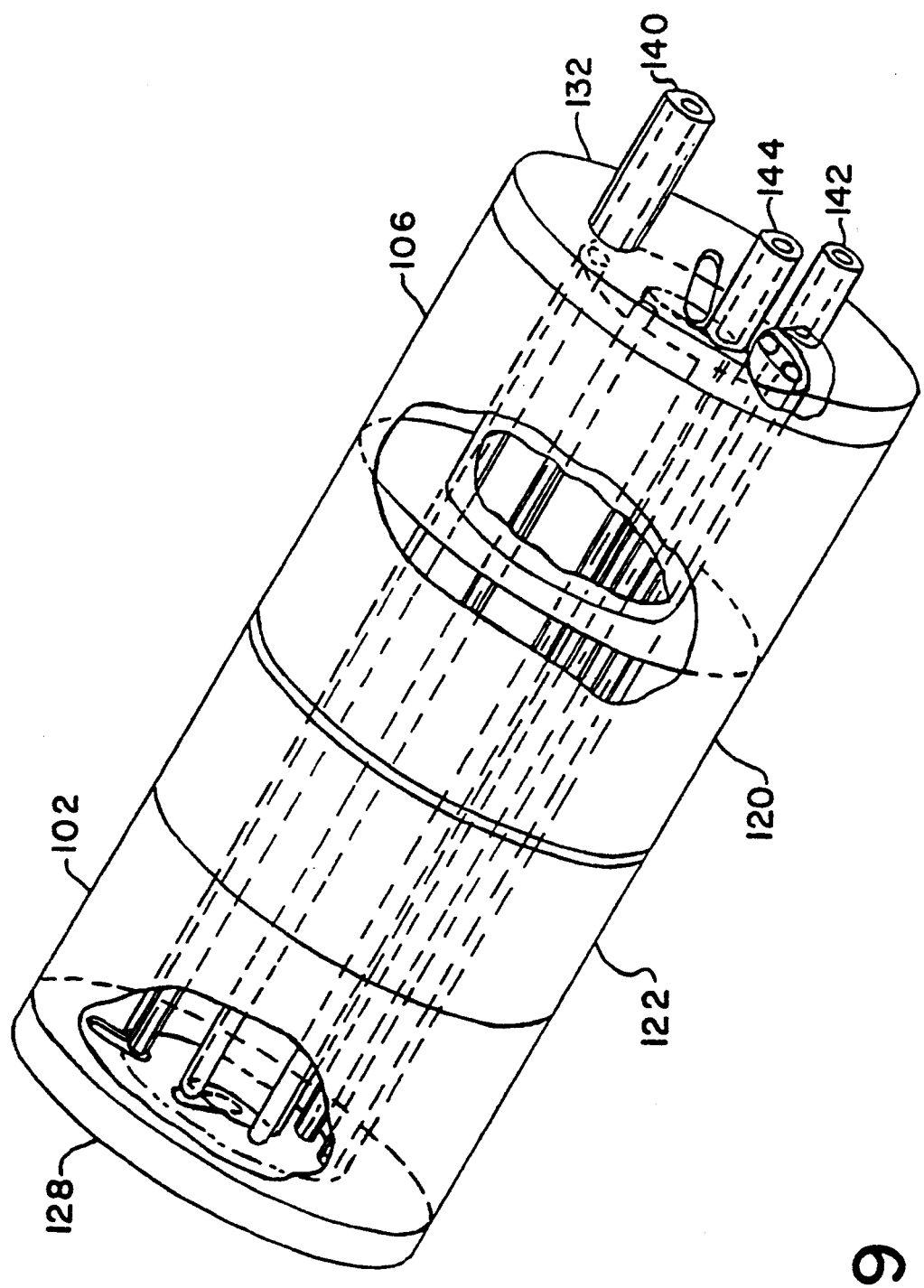
FIG. 9 is a perspective view exposed in part of an alternative RO device of FIG. 8 to illustrate generally the internal components and arrangement.
Figure 12:
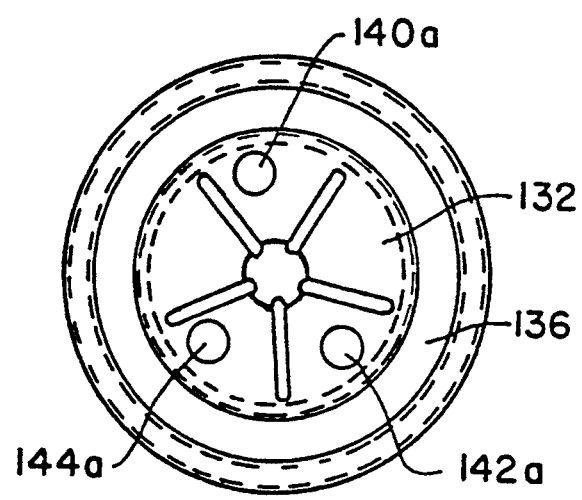
FIG. 12 is a front view of the metal top portion of cap for sealing the open end of the housing of the RO device of FIGS. 4 and 8.
Figure 12:
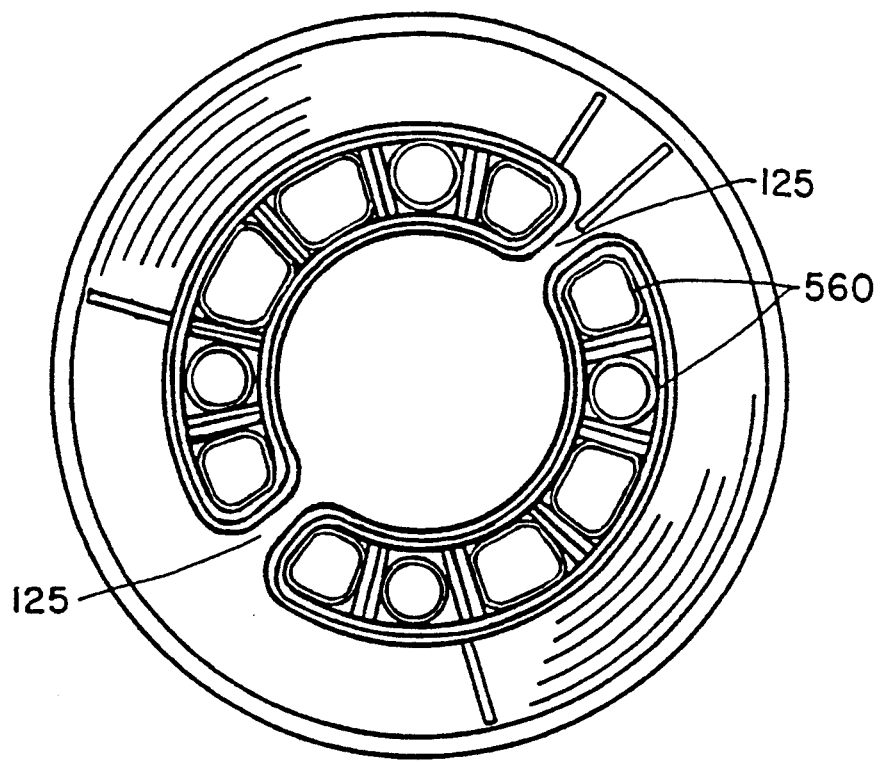
Figure 12A:
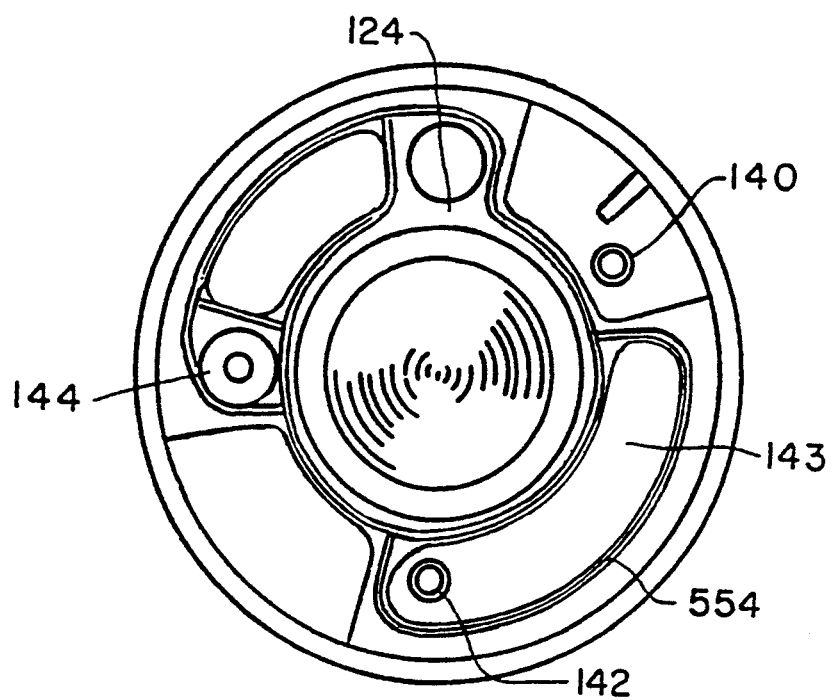
FIG. 12A is an inside view of the plastic portion of the cap of FIG. 12.

The housing 102 has a base 128 which is dimpled inwardly toward the interior of chamber 104 as shown in FIG 4. The housing 102 is open at its other end which is sealed by a cap assembly 130 that is formed of two pieces. An integral cap member 132 made of the same plastic material from which the core 106 is fabricated and an annular steel cap plate 136 which at its inner end seals about a periphery of cap member 132 and at its outer end seals in a formed manner with rolled edge 138 of the housing 102. As shown in FIG. 12, the annular steel cap plate 136 provides openings 140a, 142a and 144a for an inlet tube 140 of cap 132 which is coupled by suitable tubing (not shown) to the high pressure water from pump 20 as shown in FIG. 1; the drain outlet tube 142 and optionally 147; and a permeate or purified water outlet 144 as shown in FIGS. 9, 12A and 5. The radial ribs of the annular steel cap plates 136 are optional and are not required. The core 106 contains a hollow space 146 to receive therein activated carbon 145 which is held in place between depth filters 148 adjacent the base 128 and 150 which is adjacent the cap 132.

As shown in FIGS. 7 and 14, a first RO multilayer subassembly 21 at one end 212 can be affixed in a longitudinal slot 214 from which the multilayer subassembly 210 is spirally wrapped around the core 106. This first multilayer subassembly comprises a porous permeate carrier layer 110 and a first RO membrane layer 112. A second RO multilayer subassembly 216 can be affixed in a second longitudinal slot 218 and is also spirally wrapped around in the same direction as the aforementioned RO multilayer subassembly 210. This second RO multilayer assembly 216 comprises a feed water mesh layer 114 and a second RO membrane layer 116. At the other end of the membrane multilayer subassembly 210, the edge is kept open to allow tap water under pressure to enter. The dotted circle 220 indicates the actual radius of the complete RO multilayer assembly when wound onto the core 106.

The RO device, as shown in FIG. 4, also includes a pressurized container 166 which is generally cylindrical having a closed end 168 resting adjacent the dimpled end of base 128 and secured by a hot melt glue bead 169. The other end of pressurized container 166 is open and is dimensioned so as to receive the rolled RO second stage 122 therein. The core 106 is sonically welded to the inner base wall of the pressurized container 166. An O-ring 170 provides additional sealing to facilitate the potting of glue seal 119 which is adjacent the glue seal 118 and the inner wall of pressurized container 166. If desired, additional O-rings can be provided as well as other sealing means according to methods known to those of the sealing art. For example, an adhesive seal can be provided next to the O-ring above the glue seal 118 and below the O-ring after assembly within the pressurized container 166. In this manner, the second stage 122 is fluidly sealed from the first stage 120. The depth filter 148 is pressed in contacting relationship with a bead 172 which helps to seat the core 106 within the pressurized container 166. However, the passageways 125 are kept spaced from the base of pressurized container 166, as shown in FIG. 4 and 12B so that the fluid communication of those passageways is maintained with a chamber 174 formed therein.

As shown in FIG. 7, the core 106 has additional passageways 222 which are simply provided to lighten the weight of the core 106 and do not provide any operational function in the RO device.

In a preferred configuration, a small RO device may have an effective RO membrane surface for each of the stages 120 and 122 of about 0.5 square feet to about 1.5 square feet. A large RO device may require substantially more surface area ranging up to industrial sizes of hundreds of square feet. The rejection rate of the first stage is at least 90%. The rejection rate of the second stage is at least 60%. The overall performance of both stages in combination will be at least 96% rejection. The operating pressures across the membranes of the first and second stages are preferably about 125 psi each. The dimension of the housing 102 of the RO device is preferably about 7 inches in length, 2.3 inches in diameter. The dimension of the hollow core 106 of the RO device is preferably about 6.3 inches in length and about 1.25 inches in diameter.

Figure 6:
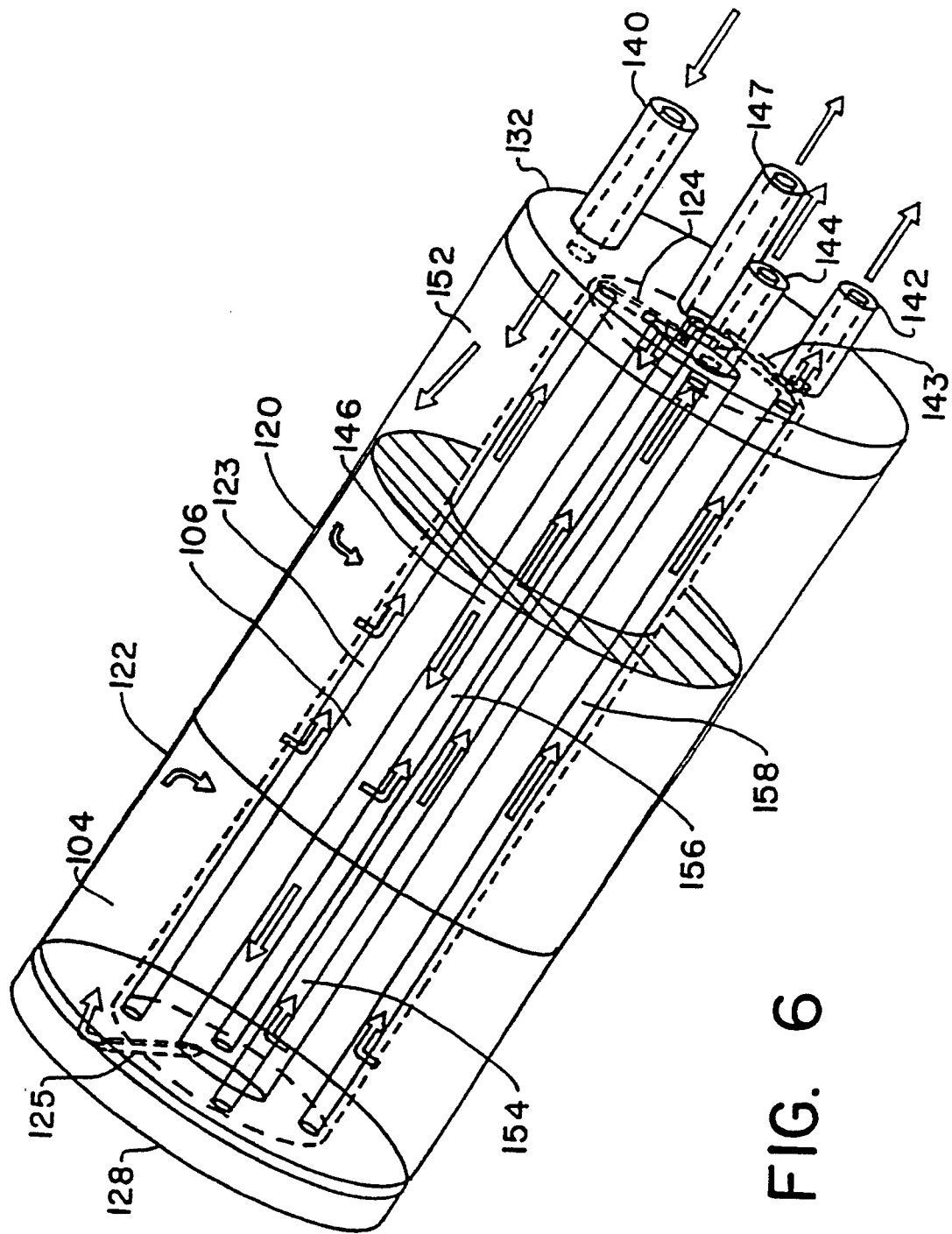
FIG. 6 is a perspective view exposed in part of the RO device of FIG. 4 to illustrate the various fluid flow paths.

In operation, the various fluid paths of the RO device are illustrated in FIG. 6, which shows that pressurized tap water enters through inlet 140 and thereafter through passageway 152. Upon entering the first stage 120, the pressurized water passes through the RO multilayer assembly. The first portion of purified water from the tap water is passed into the longitudinal passageway 123 and toward the cap member 132 and thereafter is directed by guide 124 through depth filter 150 (See FIG. 4) into the hollow space 146 containing activated carbon 145. Upon passing through the length of the hollow space 146, the now chemically purified water passes through depth filter 148 (See FIG. 4) and then through guide 125 to the chamber 104 from which the chemically purified water enters in the RO multilayer assembly of the second stage 122. Upon further filtration within second stage 122, the finally purified water passes into passageway 154 and exits through permeate outlet 144. The drain water from the first stage 120 enters into passageway 156 and then through restrictor 224 as indicated in FIG. 7 and described below in FIGS. 28-31. The second stage 122 enters into a passageway 158 and then through restrictor 226 as indicated in FIG. 7 and described below in FIG. 28-31. The fluid from restrictors 224 and 226 combine within guide 143 and subsequently drains through outlet 142. Alternatively, the fluid from the first stage restrictor 224 can drain directly through optional outlet 147 and the fluid from the second stage restrictor 226 can drain directly through outlet 142 as shown in FIG. 6.

An alternative embodiment of the RO device according to the present invention is illustrated in FIGS. 8-11, wherein structural features common to the embodiment shown in FIG. 4 are depicted by the like number. The main difference in construction from that shown in FIG. 4 is that the first stage 122 is away from the inlet 140 and is fitted against the inner wall of the pressurized container 166 and the second stage 120 is closest to the inlet 140.

Figure 10:
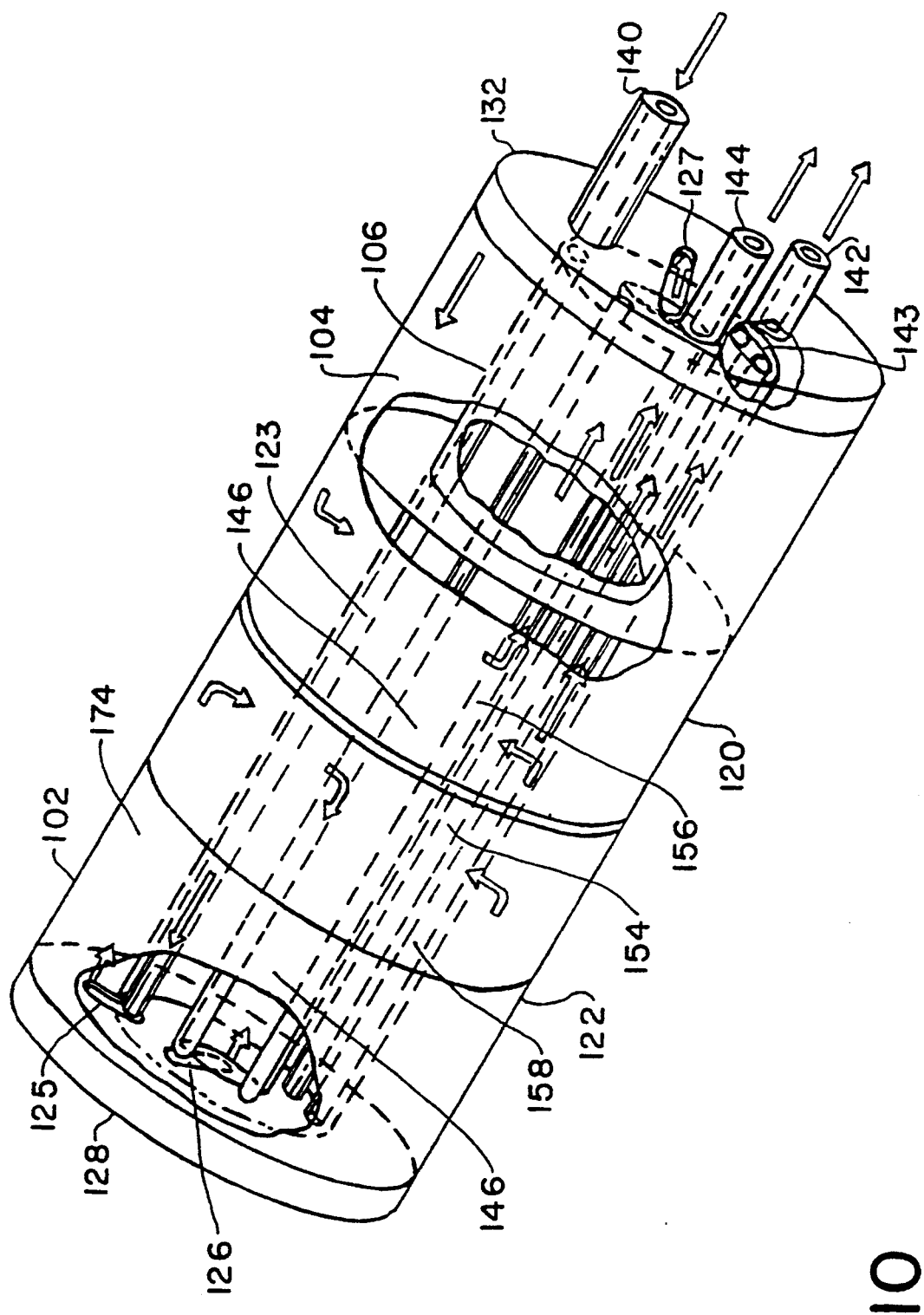
FIG. 10 is a perspective view exposed in part of an alternative RO device of FIG. 8 to illustrate the various fluid flow paths.

In operation, the various fluid paths of the RO device are illustrated in FIG. 10, which shows that pressurized tap water enters through inlet 140 and thereafter through passageway 123 within core 106. Upon approaching the base 128 of pressurized container 106 the pressurized water enters through guide 125 into passage chamber 174 and thereafter into the RO multilayer assembly of the first stage 122. The first portion of purified water from the tap water is passed into the longitudinal passageway 146 and back toward the base 128 which thereupon admits through guide 126 the first purified portion into the hollow space 146 containing activated carbon 145 within the hollow core 106. Upon passing through the length of the hollow core 106, the now chemically purified water enters the chamber 104 through guide 127 from which the chemically purified water enters into the RO multilayer assembly of the second stage 120. Upon further filtration within second stage 120, the finally purified water passes into passageway 156 and exits through outlet 144. The drain water from the first stage 122 enters passageway 158 and then through a restrictor as described below in FIG. 28-31. The drain water from the second stage 120 enters passageway 154 and then through another restrictor. The fluid from both restrictors combine within guide 143 and subsequently drains through outlet 142. Alternatively, the fluid from the first stage restrictor can drain directly through another outlet (not shown) and the fluid from the second stage restrictor can drain directly through outlet 143.

Figure 8:
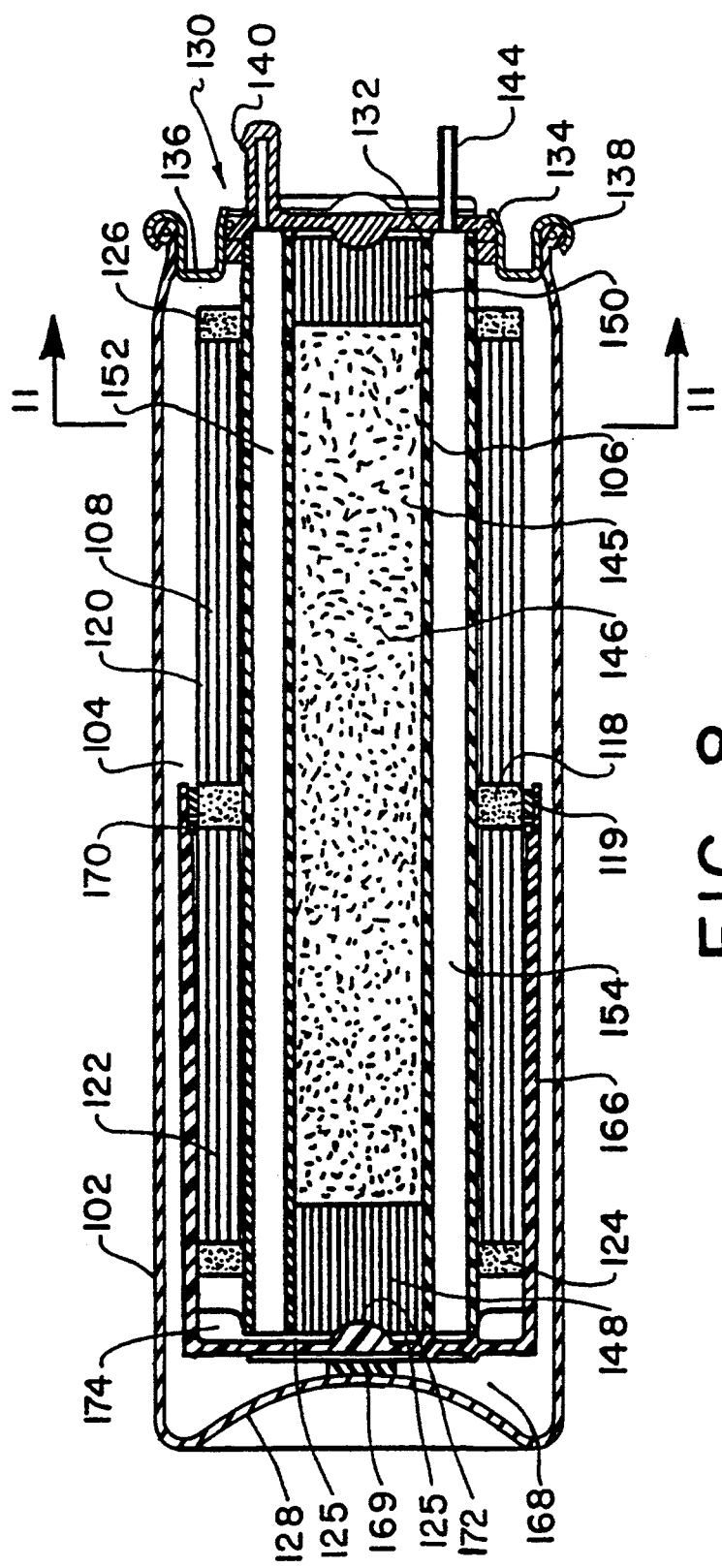
FIG. 8 is a cross sectional view of an alternative embodiment of the RO device according to the present invention.
Figure 11:
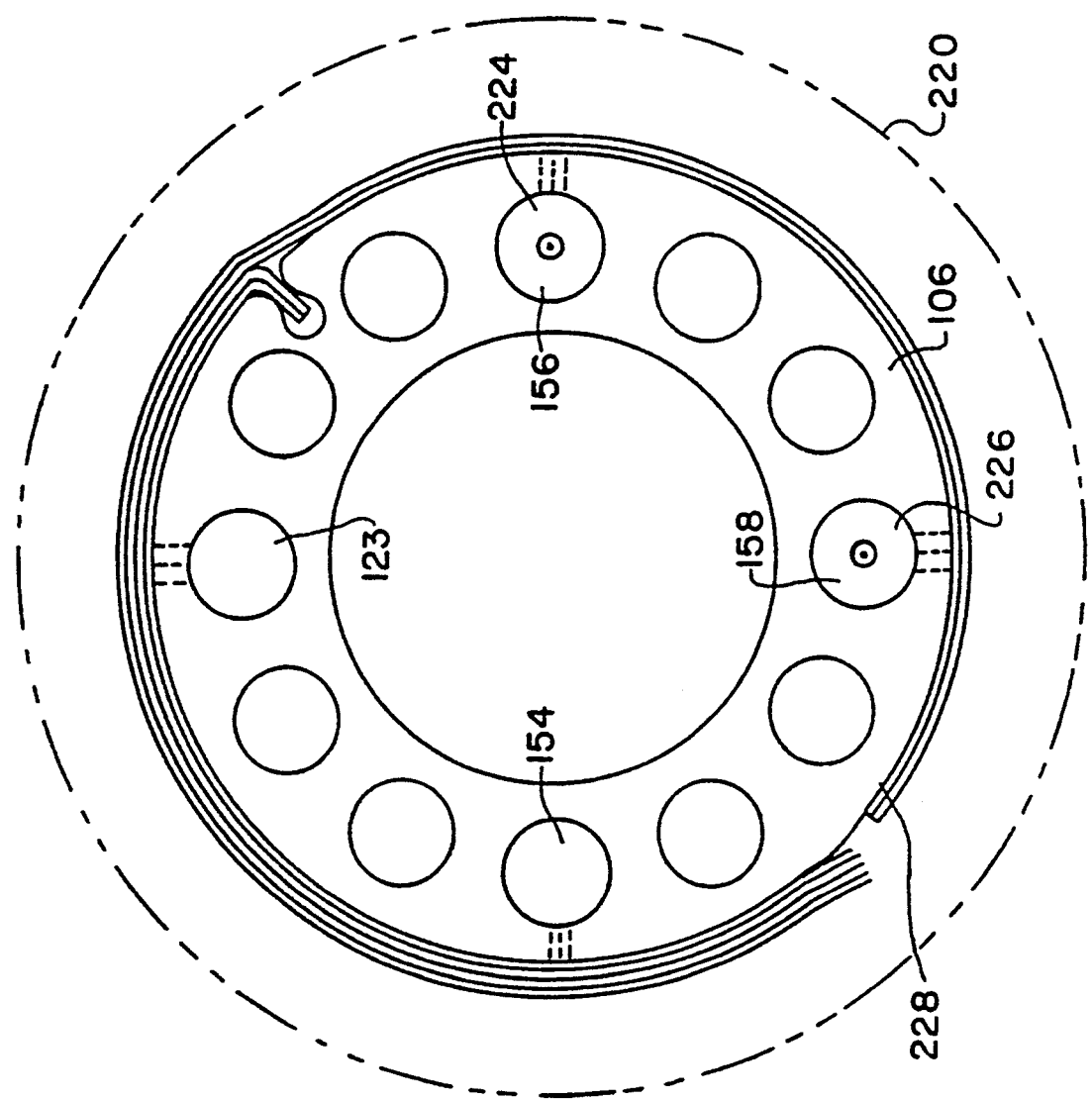
FIG. 11 is a cross sectional end view taken along the lines 11—11 of FIG. 8.
Figure 13:
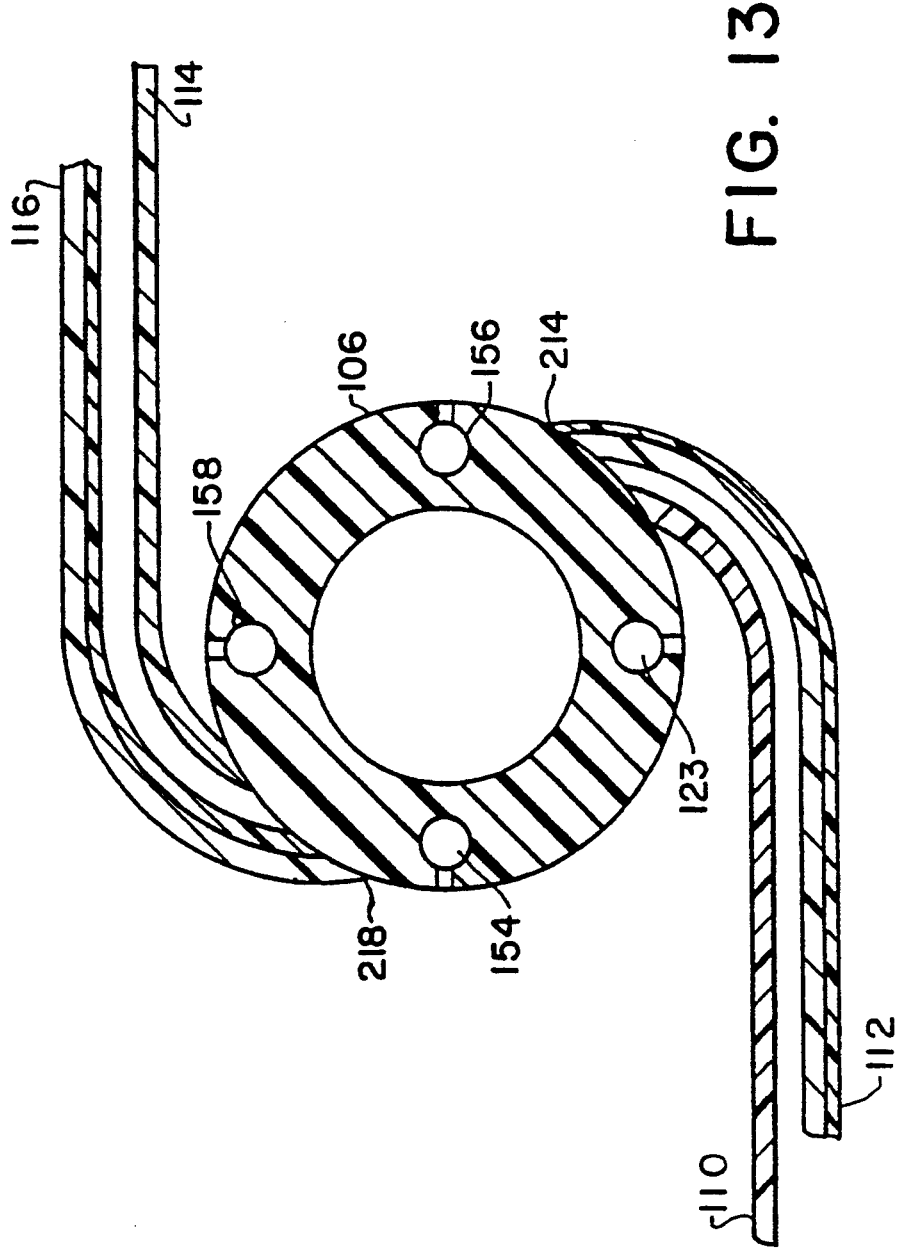
FIG. 13 is a transverse cross sectional view of the RO multilayer assembly prior to winding about the core of the RO device of FIGS. 4 and 8.

In both of the above embodiments shown in FIGS. 4 and 8, the RO multilayer assembly which is wound about the hollow core 106 is attached onto the core 106 by means of two slots 214 and 218 as shown in FIGS. 7 and 13. Preferably, one or more of the ends of the RO multilayer assembly is attached to the hollow core 106 by means of an adhesive strip 228 without placing the end into any slot as shown in FIG. 11. The RO multilayer assembly is thereby divided into two parts in its attachment to the core 106. FIG. 14 schematically illustrates the various layers of the RO multilayer assembly. As shown in FIG. 13, the first part which is attached to slot 218 comprises a porous mesh layer 114 and a second RO membrane layer 116. The second part which is attached to slot 214 comprises a porous permeate layer 110 and a first RO membrane layer 112. In operation, the unpermeated tap water is drained out from the porous mesh layer 114 and through passageways 158 and 156 within core 106 to drain outlet 142. The purified water which has permeated through the RO membrane layer 112 and 116 passes from the porous permeate layer 110 through passageways 123 and 154 within the core 106 and to permeate outlet 144.

When the multilayer is wound about the core, the RO multilayer assembly is configured as shown in FIG. 14. The first and second RO membrane layers 112 and 116 are faced in opposite directions from each other because of the structure of the RO membrane layer which is shown in FIG. 15. Adhesive beads 206 are disposed against the porous mesh layer 114 and the porous permeate layer 110 as shown to form the RO multilayer assembly. The RO membrane layers 112 and 116 comprise a nonporous, semipermeable membrane 200 an ultrafiltration membrane 202 and a polyamide cloth 204 as shown in FIG. 15. The RO membrane layers 112 and 116 in FIG. 14 illustrate the relative position of the nonporous, semipermeable membrane 200 with respective to the other layers. Specifically, the nonporous, semipermeable membrane layers of the RO membrane layers 112 and 116 are adjacent to the porous mesh layer 114.

Figure 19:
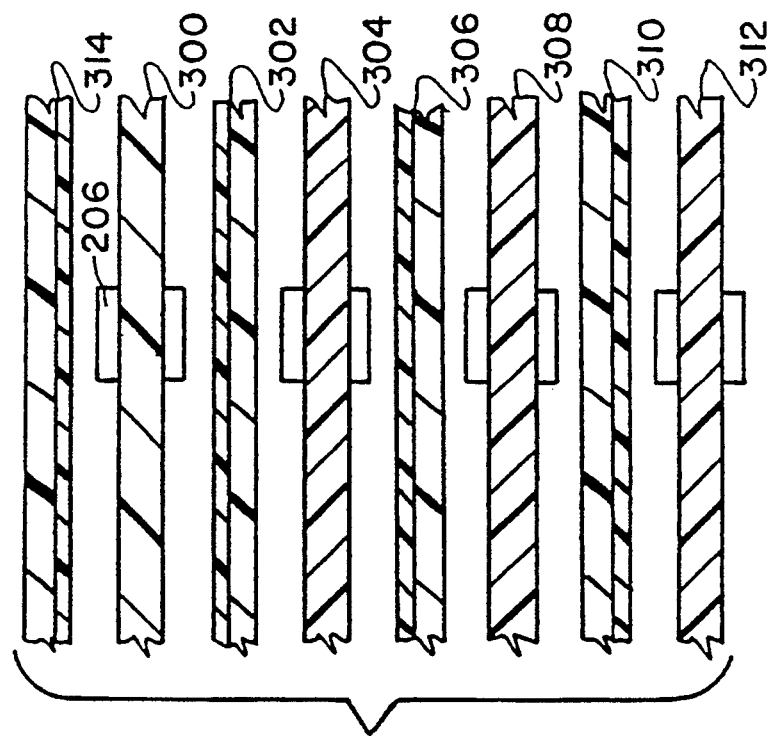
FIG. 19 is an exploded cross sectional view of the RO multilayer assembly of FIG. 18.
Figure 16:
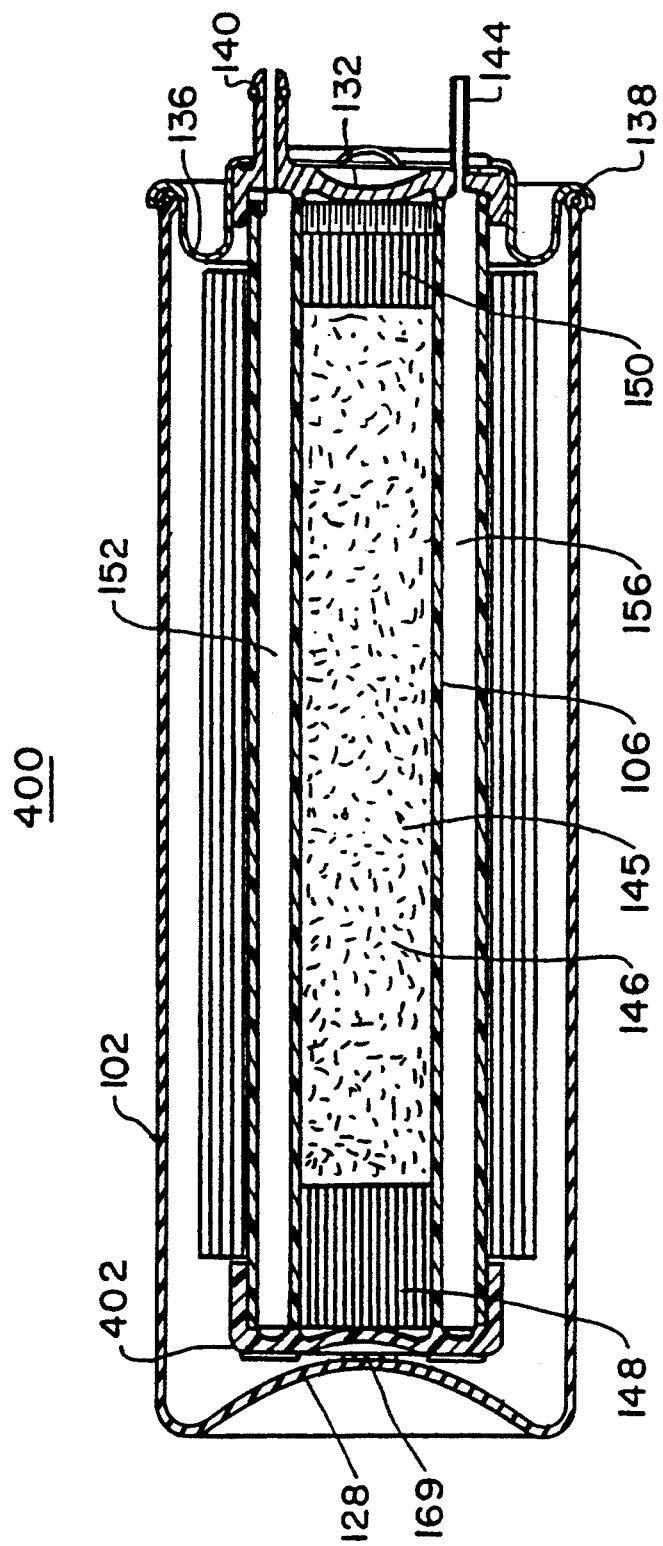
FIG. 16 is a cross sectional view of still another embodiment of the RO device according to the present invention.
Figure 17:
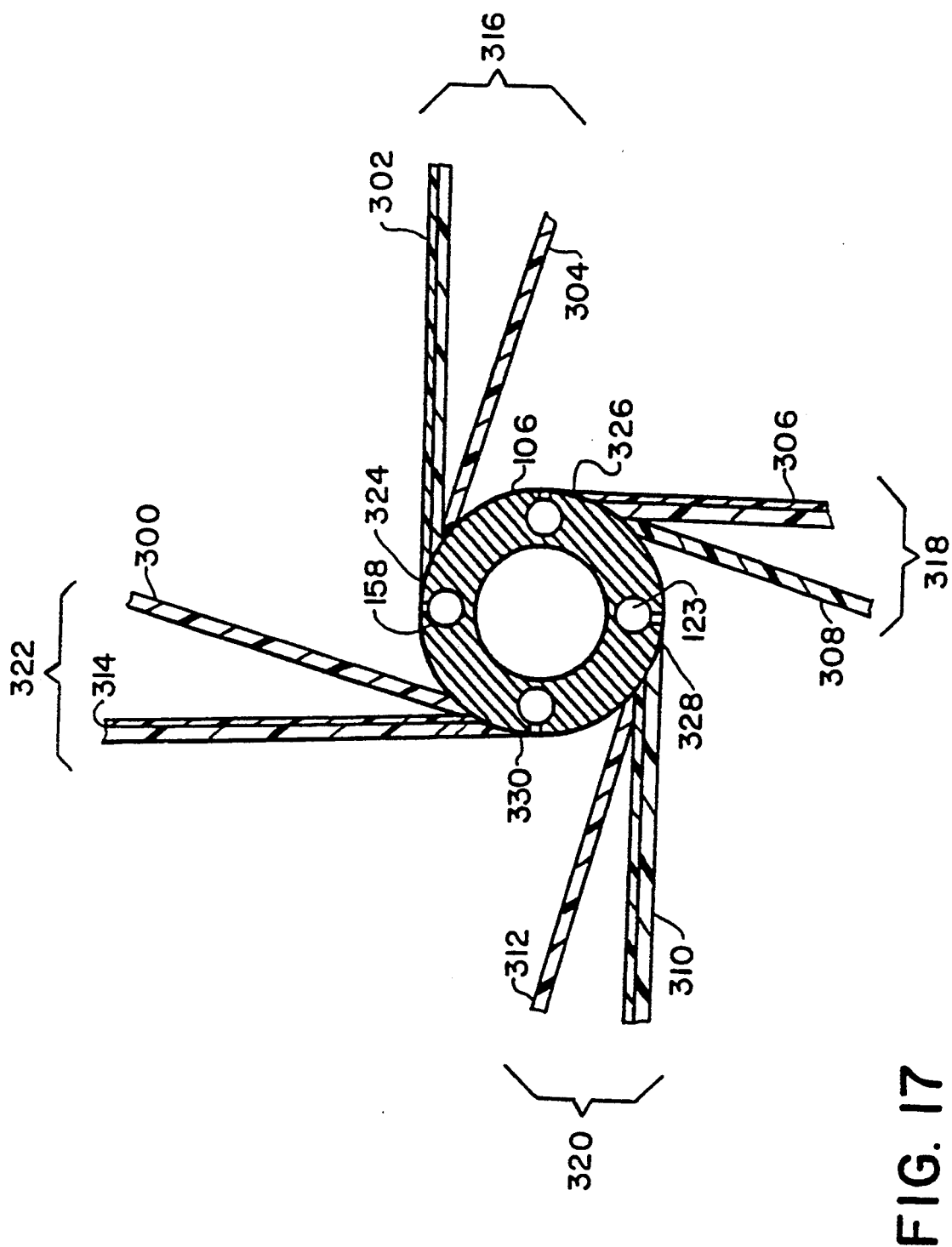
FIG. 17 is a transverse cross sectional view of the formation of the RO multilayer assembly of the RO device of FIG. 16.
Figure 18:
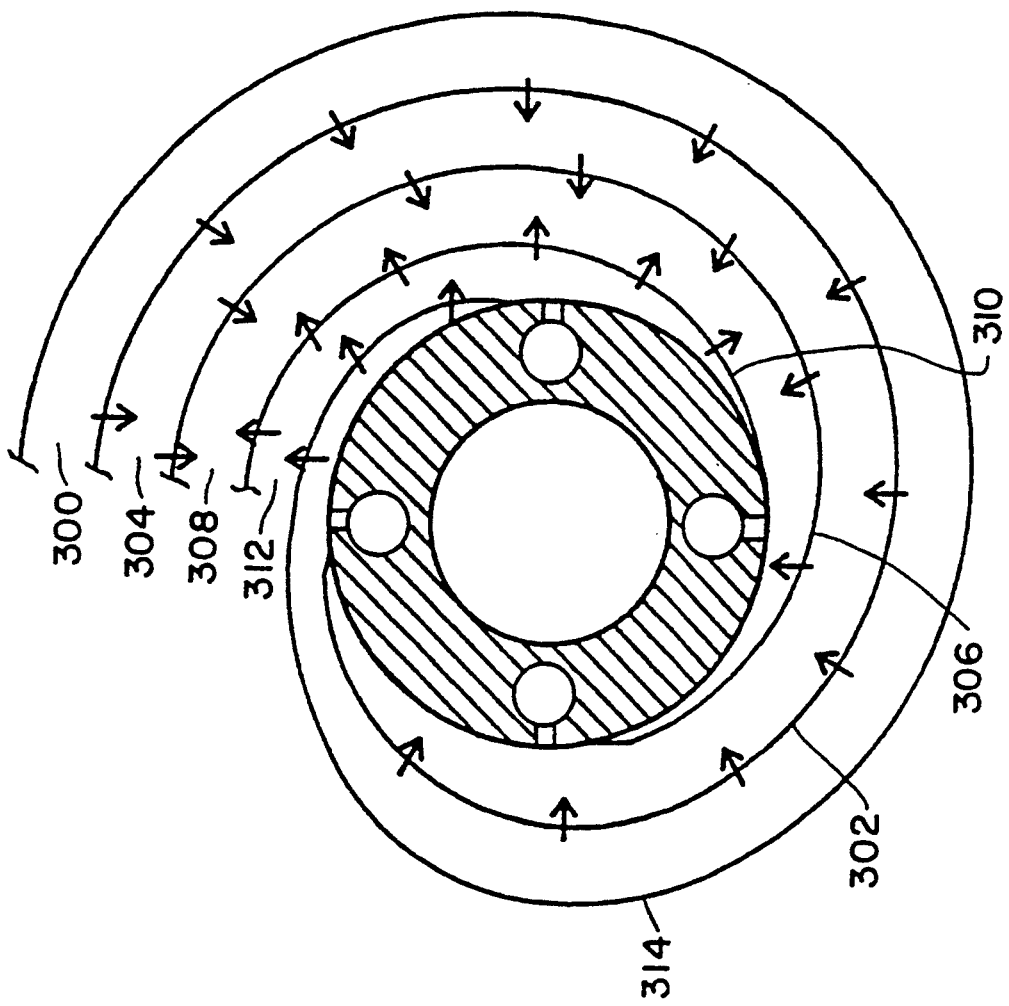
FIG. 18 is a cross sectional view in the opposite direction of FIG. 17 of the RO multilayer assembly of the RO device of FIG. 16 in an assembled configuration and illustrating the fluid flow paths.

Another alternative embodiment of the RO device according to the present invention is illustrated in FIG. 16, wherein structural features common to the embodiment shown in FIG. 4 are depicted by like number. As shown in FIG. 16, the RO device 400 has a central core 106 which is positioned within an end base cap 402 and secured to adjacent base 128 of housing 102 by hot melt glue bead 169. As shown in FIG. 17, four RO multilayer subassemblies 316, 318, 320 and 322, are affixed in longitudinal slots 324, 326, 328 and 330, respectively, in core 106. Alternatively, the ends of the subassemblies may be attached to the core by adhesive beads. RO multilayer subassembly 316 is formed of a nonporous, semipermeable membrane layer 302 and a porous permeate layer 304. The RO multilayer subassembly 318 is similarly formed of a nonporous semipermeable membrane layer 306 and a porous permeate layer 308. Likewise, the RO multilayer subassembly 320 is similarly formed of a nonporous semipermeable membrane layer 310 and a porous permeate layer 312. The RO multilayer subassembly 322 is formed of a nonporous semipermeable membrane layer 314 and a porous mesh layer 300. Unpermeated tap water exits through passageway 158 and drain outlet 142 and sterilized water exits through passageway 123 and permeate outlet 144. As shown in FIG. 18 which is taken in the opposite direction of FIG. 17, the RO membranes 302, 306, 310 and 314 are spirally wound around the core 106 as well as each other. Alternatively, FIG. 18 represents an RO configuration in which the RO membranes, if desired, can be rolled about core 106 in the opposite direction to that shown in FIG. 17. Interleafed between the RO membranes are the porous mesh layer 300 and the porous permeate layers 304, 308 and 312. When the static pressure within the porous mesh layer 300 is TP, the static pressure within the porous permeate layers 304 and 312 is ½ TP and the static pressure within the porous permeate layer 308 is about 0.05 TP. The various flow paths are shown in FIG. 18 as well. In operation, the alternative embodiment of the RO device of FIG. 16–19 is substantially the same as that described with reference to the RO device illustrated in FIGS. 4 and 8. However, the alternative RO device of FIG. 18 passes the water from the high pressurized source through the two RO stages which are formed of the four RO multilayer subassembly of FIG. 17 before passing through the activated carbon 145 contained in the hollow space 146 within core 106 between depth filters 148 and 150. An exploded cross-sectional view of the RO multilayer assembly of FIG. 18 is shown in FIG. 19. Adhesive beads 206 are disposed against the layers as shown to form the RO multilayer assembly.

The activated carbon serves to remove chloramine as well as dissolved gases from the tap water. In the event that the water supplied to the RO device is already free of chloramines, then there is no need to chemically treat the water. In addition, chemical treatments can be utilized for removal of other chemical species as well. Both the semi-permeable membranes in the RO device of FIG. 4 and the alternative embodiments of FIGS. 8 and 16 are preferably formed of polyamide. However, other semi-permeable membrane layers can be utilized as well.

In both embodiments of the RO device as illustrated and described herein, the RO membranes are formed in a spiral configuration so as to maximize the velocity of tap water across the membrane and to minimize the concentration polarization at the membrane surfaces within as small and compact a housing as possible. This avoids the need to provide for extensive lengths of housing to enclose RO membranes as found in typical applications.

Yet another alternative embodiment of the RO device according to the present invention is illustrated in FIG. 20. The RO device 702 includes a generally cylindrical housing 704 having an end cap 706 in which is disposed centrally an inlet port 708 that is fluidly coupled to the source of water to be purified. The other end has a seal cap 710 that is screwed on by threads which engage cooperating threads 712 on the adjacent end portion of housing 704. The seal cap 710 has a waste outlet 714 and a permeate outlet 716. Positioned internally within the housing 704 is a core 701 that is generally cylindrical and is formed of three longitudinal passageways as shown in FIG. 20A. Two of the passageways 720 and 722 are of like shape and together form half of the core 701. The remaining passageway 724 includes activated charcoal for the same purposes as discussed above in connection with the prior embodiments. Passageway 720 is coupled through outlet 714 for passage of waste water. The other like passageway 722 provides for passage of permeate and is coupled to the outlet 716 in seal cap 710. A first RO stage 726 is positioned within chamber 728 formed within housing 704. The second stage 729 is positioned within housing 704 in chamber 730 adjacent seal cap 710. The first and second stages are connected through a restrictor 705. The restrictor 705 is designed to adjust the backpressure within the first and second stages 726 and 729 so as to provide the desired water flow rate across the membranes. The first and second RO stage's 726 and 729 are separated by a core support carrier 732 which is snugly fit within housing 704. The support carrier 732 has a U-shaped channel 734 that extends along the periphery of carrier 732 to receive an O-ring 736 as shown in FIG. 20. In operation, water enters through port 708 and into chamber 728 wherein it enters into the first RO stage 726. After filtration, the filtered portion of the water passes through radial openings 741 in core 701 into passageway 724. Upon passing through the activated charcoal 718 within passageway 724, the partially filtered water passes through radial opening 740 in core 701 into chamber 730 and from there into the second RO stage as shown in FIG. 20. Upon further filtration, the permeate passes out through outlet 716. The waste water from the first stage passes through radial openings 742 into the return passageway 720 and from the second stage through radial opening 744 also into the waste passageway 720 and finally out the waste outlet 714.

Figure 21:
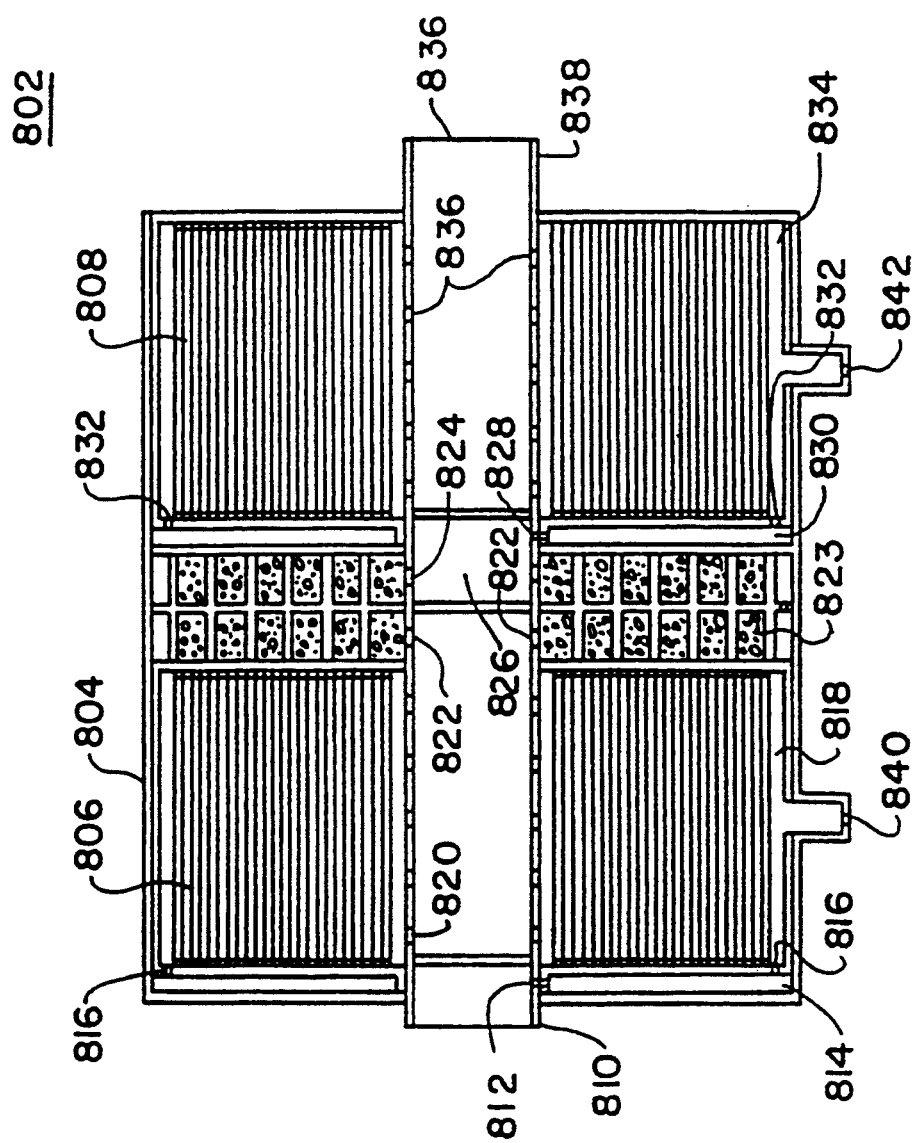
FIG. 21 is a cross sectional view of still another alternative embodiment wherein the inlet port is generally transverse to the outlet ports.

In yet another alternative embodiment of the RO device according to the present invention as shown in FIG. 21, the RO device 802 includes a cylindrical housing 804 that includes a first RO stage 806 and a second RO stage 808 which are wrapped around a central core 810. The central core 810 has an inlet port 812 through which water passes into an interior chamber 814 and thereafter through openings 816 into the chamber 818 in which the first stage 806 is positioned. Upon passing through the first stage 806, the filtered water passes through radial opening 820 in core 810 and thereafter through radial opening 822 into a central portion containing activated charcoal 823. Upon passing through the charcoal 823, the purified water passes out through radial opening 824 into chamber 826 and through radial opening 828 in core 810 through antechamber 830 and therefrom through opening 832 into chamber 834 in which the second RO stage 808 is positioned. Upon passage through the second RO stage, the permeate exits through radial opening 836 and out through port 838. The waste water from the first RO stage exits through drain port 840 while the waste water from the second RO stage 808 passes through the drain port 842.

In order to provide for proper water flow across the RO multilayer assembly 108, the cylindrical passageway tubes in core 810 are designed in accordance with the Bernoulli equation so that their diameter and length are calculated to produce a static pressure drop across both RO multilayer assemblies 108 of the first stage 806 and second stage 808. The pressure drop produces the desired water flow rate across the membranes. For example, the flow across the second membrane is less than across the first. Static pressure across the first membrane is twice that across the second. This yields a different geometry for the second restrictor. Balancing the spiral resistance with the cylindrical resistance is the key to the proper functioning of the RO Device.

Figures 30, 31:
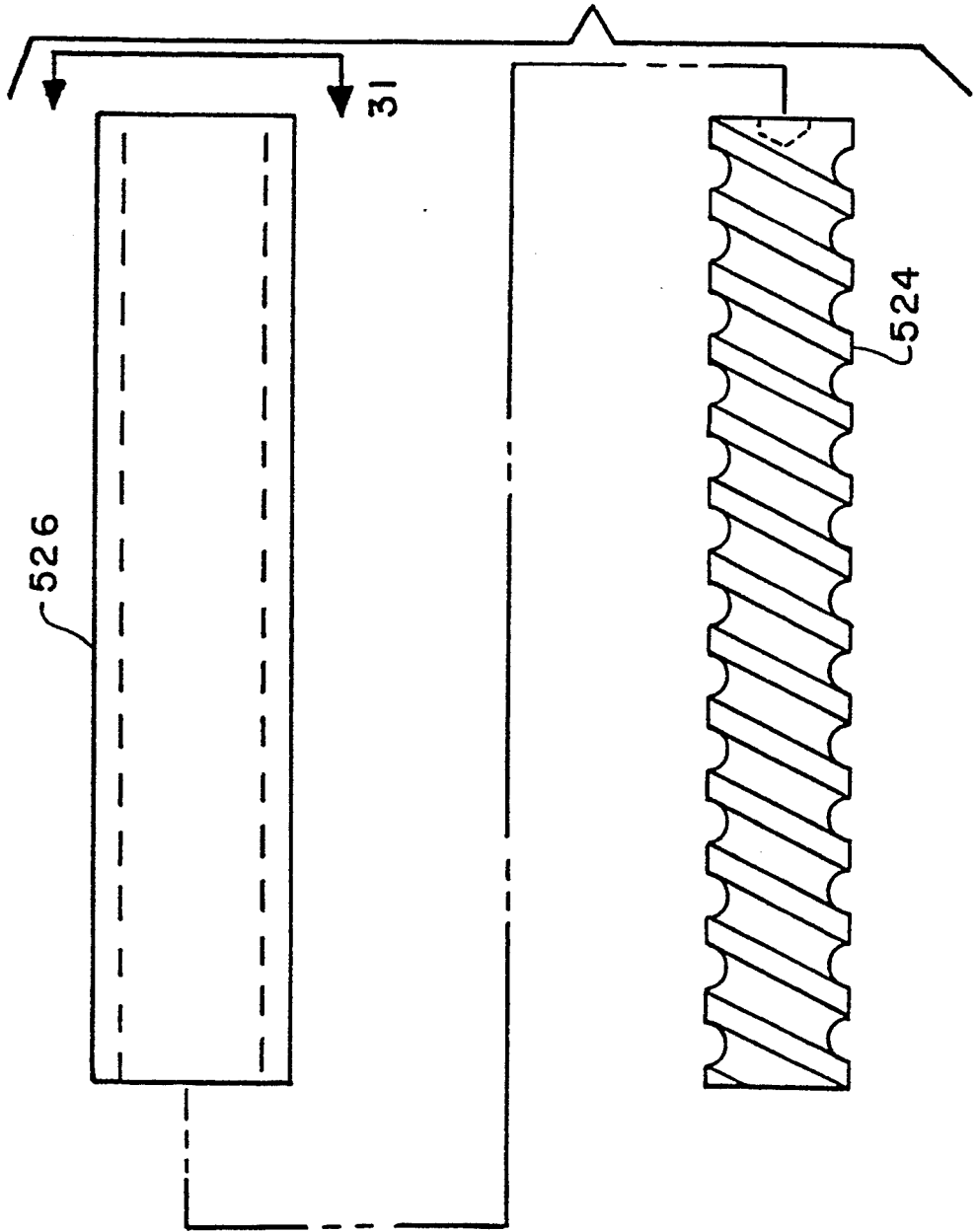
FIG. 30 is an exploded side view of an alternative embodiment of a restrictor according to the present invention.
FIG. 31 is an end view of the restrictor assembly of FIG. 30.

FIGS. 28 and 29 illustrate a linear restrictor having a barrel 522 and a needle 520 of proper internal diameter and path length to produce the required static pressure drop across both RO multilayer assemblies. FIGS. 30 and 31 illustrate a helical restrictor which serves the same function. The advantage of the helical restrictor 524 is that the pathlength along the restrictor 524 within sleeve 526 can be manually adjusted by screwing the restrictor 524 further into or out of the sleeve 526 by way of a slot 528. The dimension of the helical restrictor 524 is preferably about 1 inch in length, 0.150 inch in diameter with about 16 threads per inch and a thread width of 0.020 inch. The effective path length of such a helical restrictor 524 is therefore about 5.938 inches. The restrictors are disposed within the passageways which fluidly connects the drains of RO multilayer assemblies of the first and second stage. Alternatively, the restrictor may be placed at the outlet drain of stage one and the outlet drain port of the device.

In the operation of the present peritoneal dialysis system (PDS) 10 of the present invention, the potable water can be heated to about 40° C. before passing through the RO device 22 as shown in FIG. 1. The higher temperature increases the efficiency of the reverse osmosis process. Specifically about 600 ml/min of potable water can be heated from about 20° C. to about 70° C., preferably up to 40° C. In order to decrease the heating demand on heater 18, the heat exchanger 16 transfers heat from the waste water from RO device 22 and patient 50 to the potable water before the potable water passes through heater 18.

Figures 22, 22A:
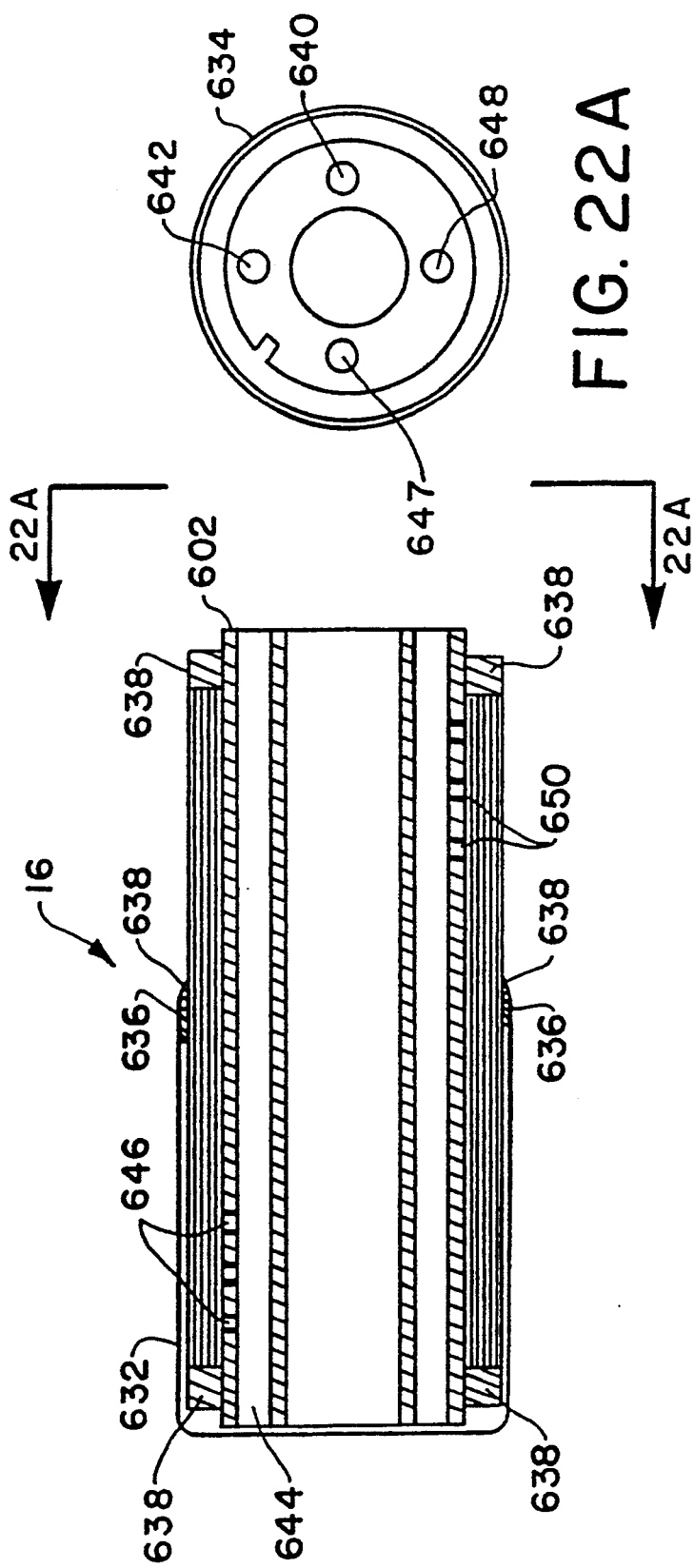
FIG. 22 is a cross sectional view of a portion of a heat exchanger according to the present invention.
FIG. 22A is an end view along lines 22A-22A of FIG. 22.
Figure 24:
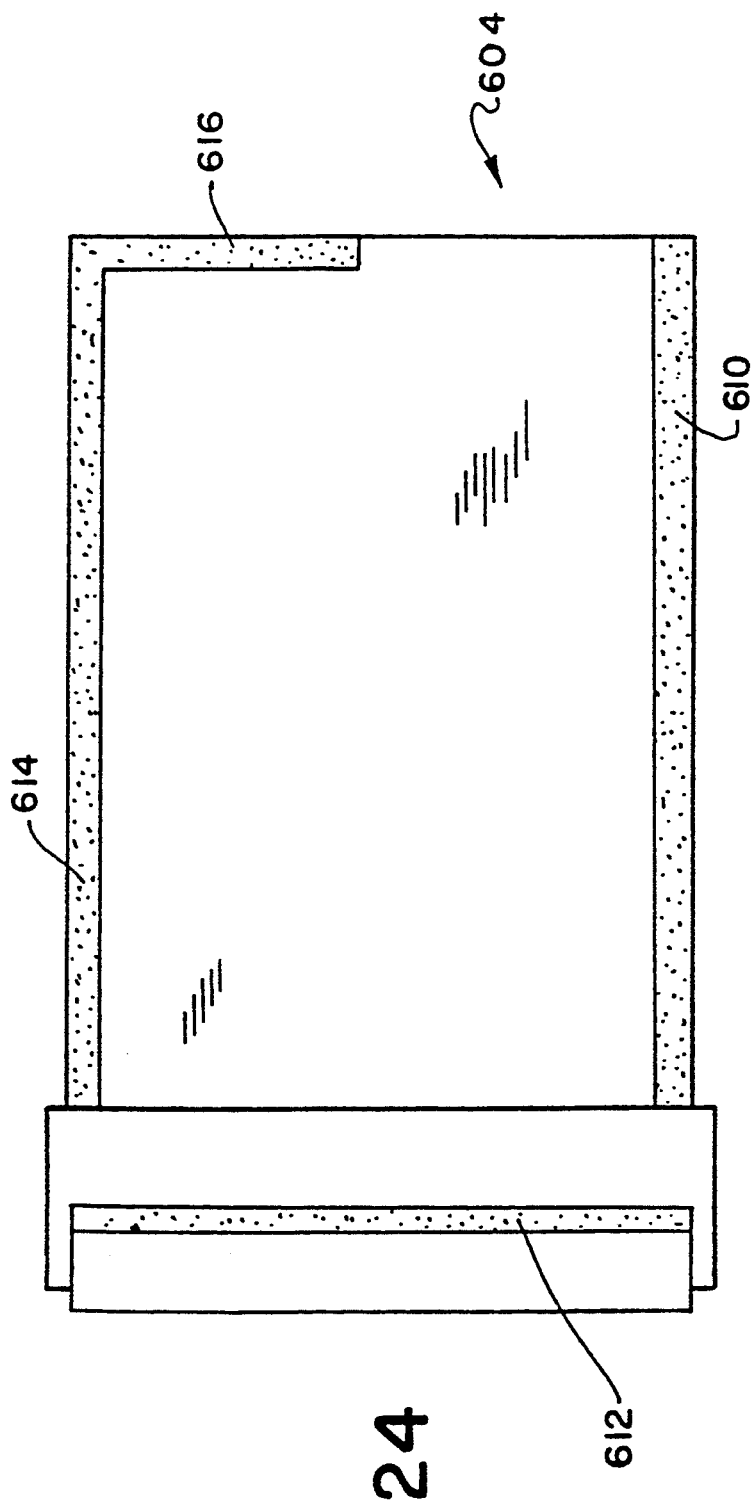
FIG. 24 is a top view of the first layer of FIG. 23.
Figure 23:
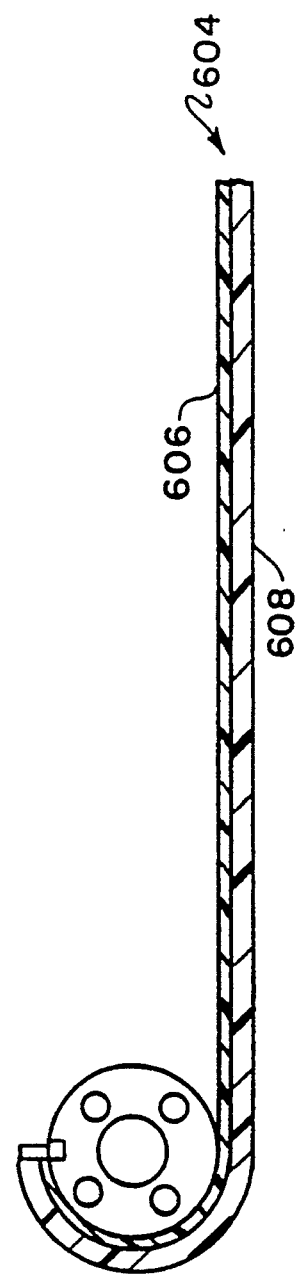
FIG. 23 is a side end view of the first layer of the heat exchanger prior to assembly about the core.

The configuration of the heat exchanger 16 is similar to that of the RO device 22 but only requires thin non-permeable membrane multilayer assemblies with porous spacers spirally wound about a hollow core 602 as shown in FIG. 22. Specifically, the heat exchanger 16 contains a first multilayer assembly 604 as shown in FIG. 23 which includes a first porous spacing layer 606 and a non-permeable membrane layer 608. Adhesive beads 610, 612 and 614, preferably of RTV silicon, are applied along the side edges as shown in FIG. 24. A partial adhesive bead 616 is applied to the free end along a portion thereof. A second multilayer assembly 618 shown in FIG. 25 includes a second porous spacing layer 620 and a non-permeable membrane layer 622 that are disposed on the first multilayer assembly 604 such that the first and second porous spacing layers 606 and 620 are interleafed between the two non-permeable membrane layers 608 and 622. Adhesive beads 624, 626 and 628, also preferably of RTV silicon, are applied along the side edges of multilayer assembly 618 as shown in FIG. 26. A partial adhesive bead 630, oppositely disposed to partial adhesive bead 616 in FIG. 24, is applied to the remaining free end of multilayer assembly 618 along a portion thereof.

As shown in FIG. 22, the first and second multilayer assemblies 604 and 618 are wrapped about core 602, preferably made of ABS plastic, and are imbedded within the pressurized container 632 which is similar to container 166 in the RO device of FIG. 4. The end cap 634 seals the heat exchanger unit 16 within a housing (not shown). An O-ring 636 helps to seal the unit 16 within the pressurized container 632. The RTV silicon sealant is shown generally in the assembled form in FIG. 22 at 638. The hot waste water enters through part 640 and cold discharge water exits through port 642 after passing through longitudinal passageway 644. Radial holes 646 in the core 602 admit the spent or cold waste water from between the membrane multilayer assemblies into the passageway 644. Cold potable water enters through port 647. Hot potable water which has received heat transferred from the hot waste water between the membrane multilayer assemblies passes through port 648 in cap 634 after exiting through radial holes 650 in core 602.

In operation, hot waste water passes through the first porous spacing layer while tap water passes through the second porous spacing layer. The transfer of heat from the hot waste water to the potable water occurs across the non-permeable membrane layers as the waste and the potable water flow spirally in a countercurrent or concurrent flow path. The porous spacing layer is preferably polypropylene mesh. The non-permeable membrane layer is preferably a polyester film such as Melinex ® or a foil, preferably metallic.

Heat transfer efficiency of the heat exchanger 16 is dependent on the membrane material used, the water flow path width, the path length as well as the amount of area available for heat transfer. Consideration of heat transfer efficiency, however, must be balanced with the unfavorable pressure drop through the heat exchanger 16. A preferred configuration has a heat transfer area of about 300 sq. inches and a pressure drop of about 4 psi at 600 ml/min flow rate.

Figure 27:
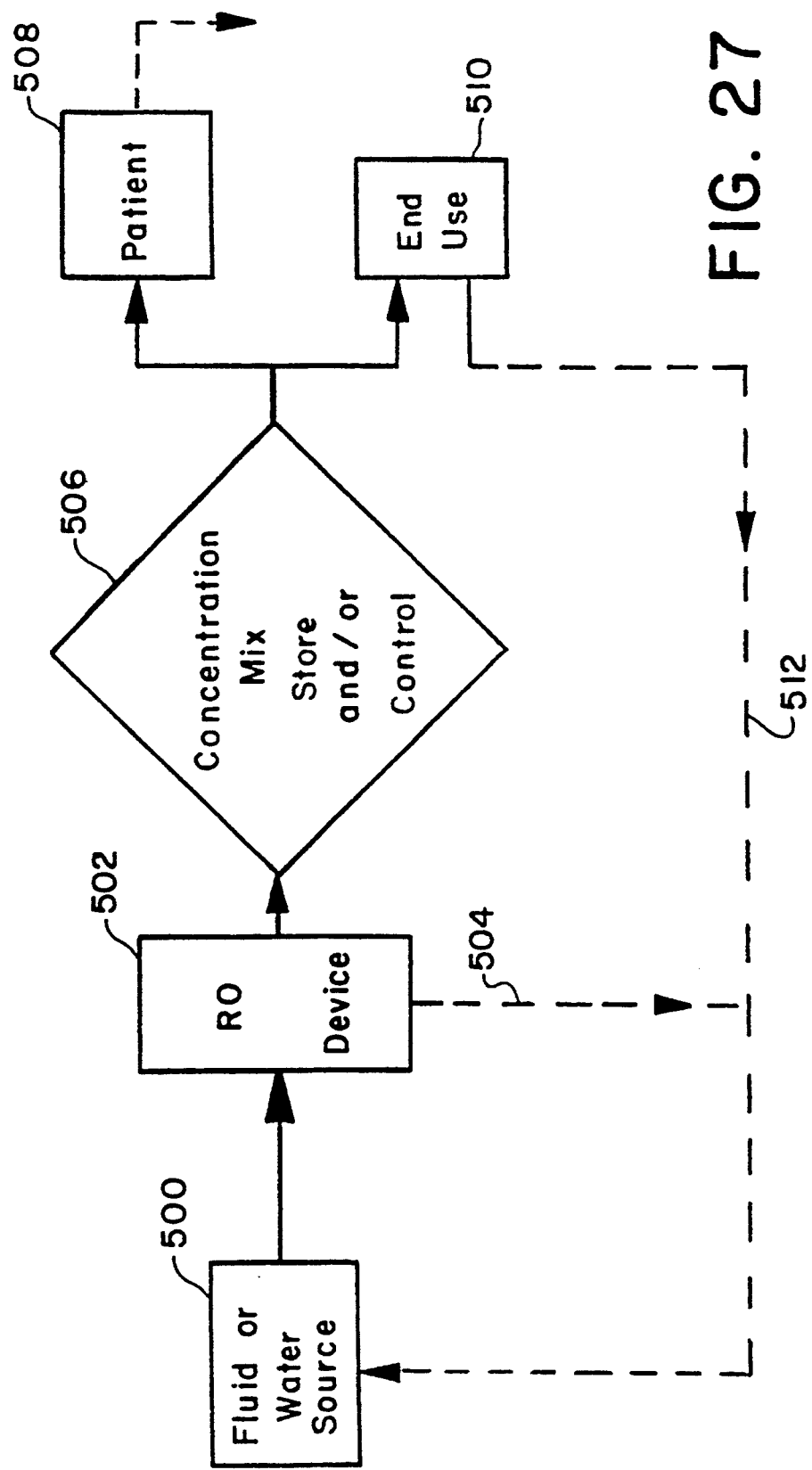
FIG. 27 is a schematic view of an alternative embodiment of a purification system employing an RO device according to the .present invention for use in an automatic peritoneal dialysis system or other application uses.

A more general illustration of the use of the RO device is presented in FIG. 27 which illustrates a source of fluid or water 500 which is passed on to a RO device 502. Here again, the waste fluid is passed on to a drain 504 while the purified fluid is passed on to a concentration, mix, store and/or control system 506. Storage can be provided in suitable bags which thereafter can be utilized when desired for the patient 508 or other end uses 510. If denied, a portion of the purified fluid after use can be returned to the source along fluid path 512. Similarly, some or all of the waste from the RO device 502 can also be returned to the source and thereafter passed on for purification within the RO device 502.

According to the preferred design, the RO cartridge may be used for three to six days during a weekly treatment and thereafter is discarded. Discarding the cartridge is necessary because of carbon contamination build-up and to avoid a sterility breach. For this reason, there is no need to sterilize while in use the RO membranes so as to remove any contaminants whether chemical or particulate as is required with present systems. In order to provide an RO cartridge suitable for home use, the RO cartridge is designed for optimization of compactness and space as well as performance so as to minimize the cost. This will enable the patient to obtain home treatment without the need to stock a large quantity of sterile water and also further avoids the need to provide for multiple hook-ups as is required in the case of CAPD treatment. Discussion of the concerns and problems relating to connection to multiple water bags is presented in an Optum ® brochure entitled "The Hands-Free Exchange For Your CAPD Patients" and U.S. Pat. No. 4,840,621 which are incorporated herein by reference.

By means of the use of a dual RO stage system, less expensive RO membrane multilayer assemblies can be utilized so as to still obtain preferably at least a 96% rejection rate. Moreover, the dual RO multilayer assemblies provide a redundancy which is medically desired in the event that one membrane fails. The drastic medical consequences of introducing pyrogen, virus or bacteria in the peritoneal cavity are thus avoided by the present RO device.

The RO device and system of the present invention accordingly overcome the problems of known filtration devices for use in peritoneal dialysis and provide sterile water solutions suitable for peritoneal dialysis and other uses as well and which can easily maintain the desired sterile conditions. Because of the modular design of the present system, the reverse osmosis device and other system components which are in contact with the water can be periodically disposed of and replaced by new sterile components. The need to have a complicated method of sterilization implemented by the user is therefore avoided.

Figure 32:
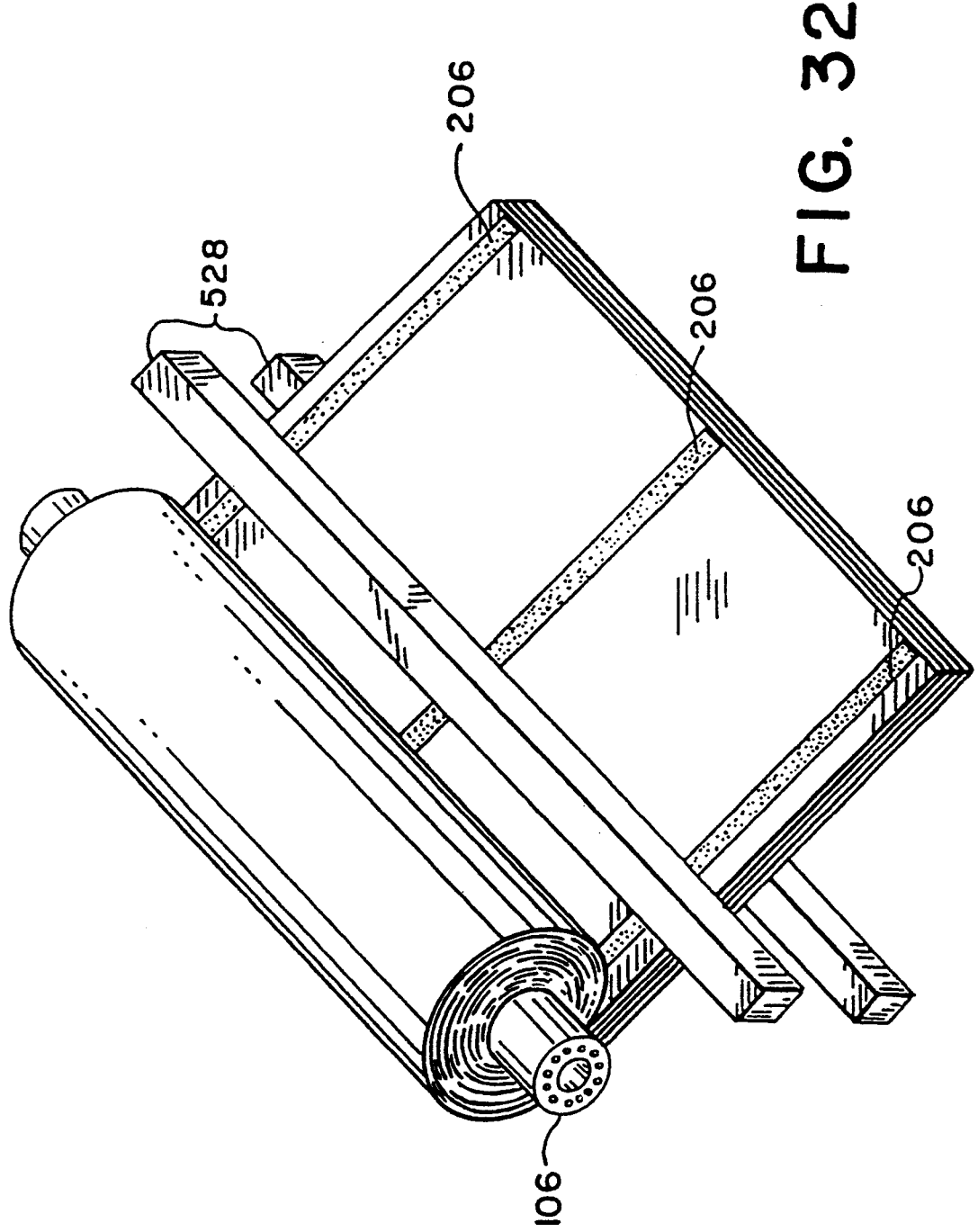
FIG. 32 is a perspective view of the application of induction heating to at least a portion of the RO multilayer assembly for heating of the adhesive bond during the assembly of the RO multilayer assembly.

FIG. 32 illustrates one efficient manner of producing the RO device of the present invention. Specifically, electromagnetically activatable adhesive beads are applied onto the porous mesh layer and the porous permeate carrier layer along the edge and the middle of the multilayer assembly as shown. The manner in which the adhesive bead is applied can be by a roller coating method in which the adhesive is heated in a pot and picked up by a transfer roller (not shown). The transfer roller then prints the adhesive strips 206 onto the porous mesh layer or the porous permeate carrier layer (see FIGS. 14 and 19) in a continuous manner as the layers move across the transfer roller. The layers are then combined and rolled onto a hollow core 106. Simultaneous to the rolling of the layers to form the multilayer assembly, the adhesive strips 206 are heated by the induction coils 528. The softened adhesive strips 206 then bond the RO multilayer assembly together as the adhesive cools within the wound layers.

A representative example of such an electromagnetically activatable adhesive may be obtained from Emabond Systems of Ashland Chemical Company, a division of Ashland Oil, Inc. and is taught in U.S. Pat. No. 3,620,875, issued Nov. 16, 1971 which is incorporated herein by reference.

Figure 33:
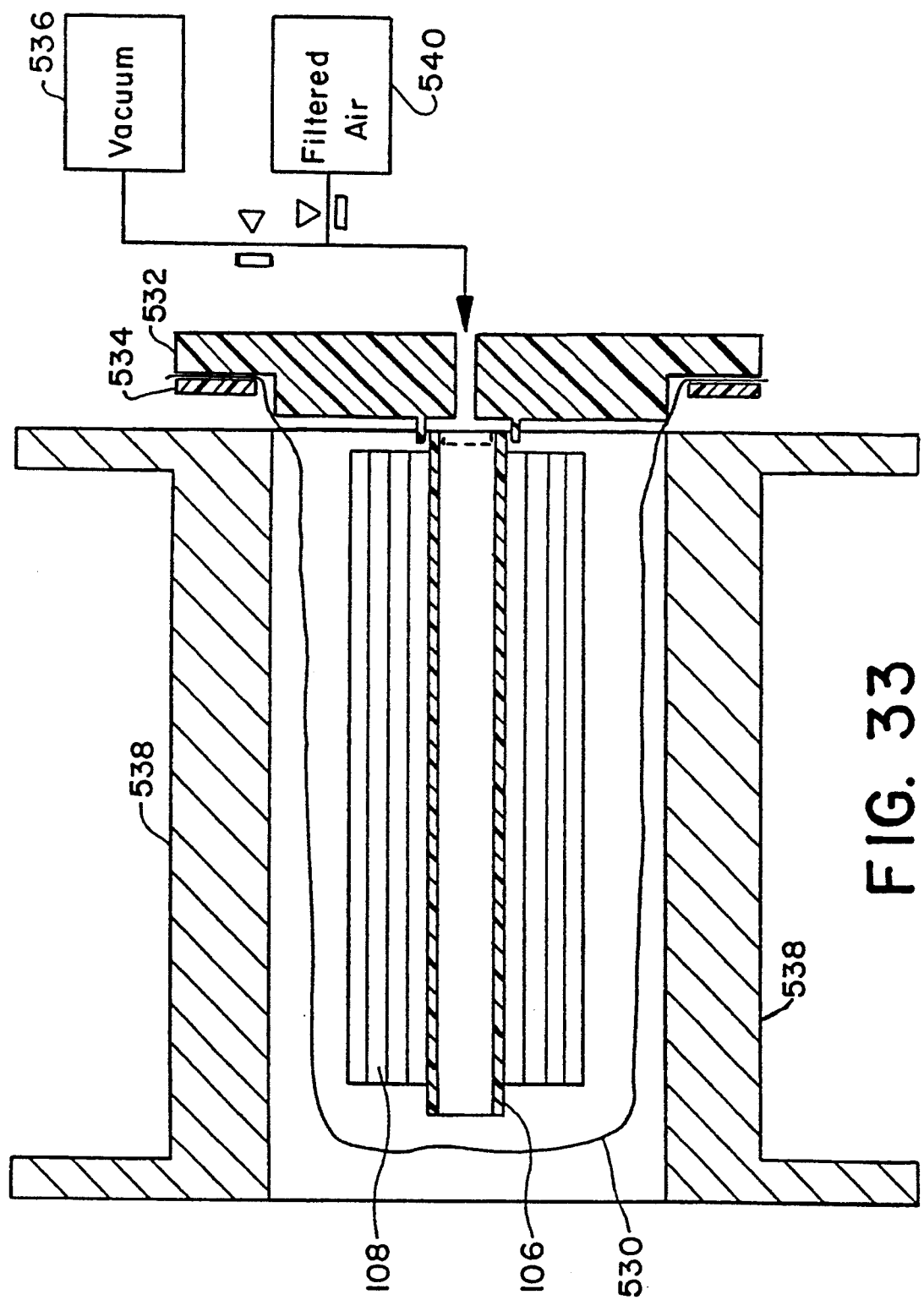
FIG. 33 is an alternative embodiment of an induction heater for use in the fabrication of the RO multilayer assembly of the RO device according to the present invention.

FIG. 33 illustrates another manner of producing the RO device of the present invention. The adhesive bead 200 has already been applied to the mesh and permeate layers of the RO multilayer assembly. The assembly 108 is subsequently wound about the hollow core 106 and then inserted into a flexible silicone bladder 530 and attached to cap 532 by ring 534. The wound assembly is then evacuated by vacuum 536 to thereby ensure close contact between the layers of the assembly and the core 106. Induction heating is then applied by coils 538 while the assembly is in the evacuated state so as to bond the layers together. The vacuum in bladder 530 is released by filtered air from 540 after cooling of the adhesive bead has occurred.

Figure 34:
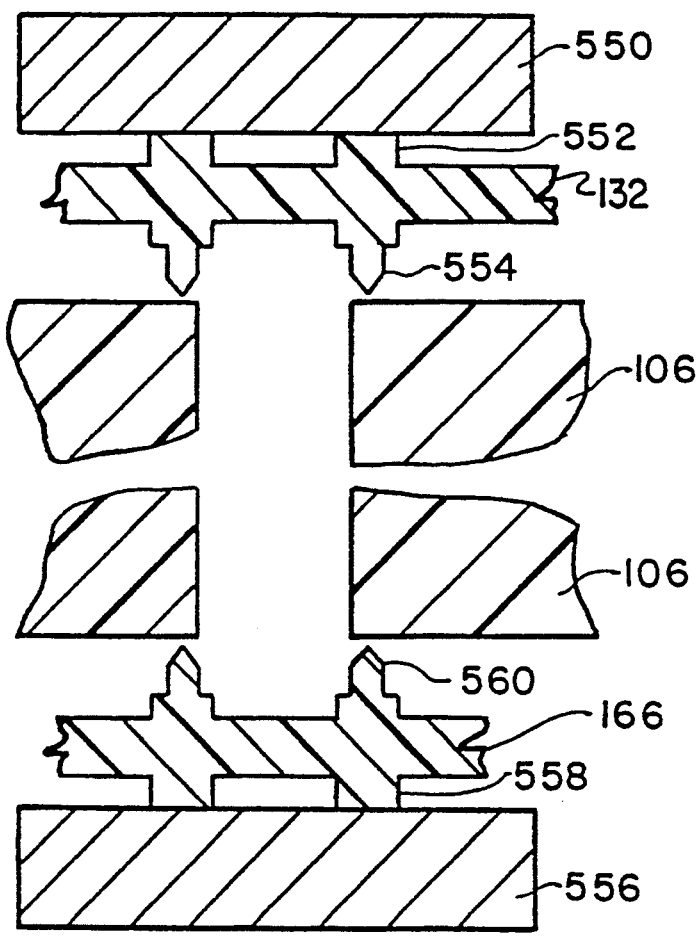
FIG. 34 is a method of sonic welding the cap to the hollow core of the RO device.

FIG. 34 illustrates a method of attaching the integral cap member 132 of the RO device to the hollow core 106 by sonic welding. The ultrasonic vibration of the sonic horn 550 is transmitted through energy transmission guides 552 to energy directors 554 so as to focus the vibration energy to the point of contact with the hollow core 106. Additionally, another sonic horn 556 is used to sonically weld the inner base wall of the pressurized container 166 to the other end of the hollow core 106 through similar energy transmission guides 558 and energy directors 560. Alternatively, the energy directors may be placed on the hollow core 106. Such directional welding can be accomplished at 20 and 40 kHz frequencies. FIGS. 12A and 12B illustrate the energy directors 554 and 560 respectively in a ridge design so as to seal the passageways of the hollow core to the integral cap member 32 and inner base wall of the pressurized container 166 as shown in FIG. 4. The pattern shown in FIG. 12A and B allows for the sealing of the passageways of the core to the guides of the cap so as to provide fluid passageway inner connections.

The ridge design of the integral cap member 132 shown in FIG. 12A is adapted to provide the RO device of FIG. 6 with the guide 124 connecting passageway 123 and hollow space 146; guide 143 connecting passageways 156 and 158 to waste drain outlet 142; the connection between inlet hole 140 and passageway 152; and the connection between permeate outlet hole 144 and passageway 154.

The ridge design of the inner base wall of the pressurized container 166 shown in FIG. 12B is adapted to the RO device of FIG. 6 so as to seal the ends of the passageways of the core 106. Guide 125 connects the hollow space 146 of the core 106 to the chamber 104 which allows the chemically purified water to enter from the hollow space 146 to the RO multilayer assembly of the second stage 122.

The present invention has been described in detail with particular emphasis on the preferred embodiments thereof. However, it should be understood that variations and modifications may occur to those skilled in the art to which the invention pertains.

We claim:

1. Method for purifying fluid from a source comprising:
   a. passing fluid in a spiral fluid manner from the source through a first spiral wound reverse osmosis means being in fluid communication with the source so as to purify at least a portion of the fluid from the source; and
   b. passing the purified first portion of fluid in a spiral flow manner through a second spiral wound osmosis means being in fluid communication with said first reverse osmosis means to receive at least some of the purified portion of fluid for further purification of at least a further portion of the fluid.

2. Method for purifying water from a source comprising:
   a. passing water in a spiral fluid flow manner from the source through a first spiral wound reverse osmosis means being in fluid communication with the source so as to purify at least a first portion of the water from the source; and
   b. passing the purified first portion of water in a spiral fluid flow manner through a second spiral wound reverse osmosis means being in fluid communication with said first reverse osmosis means to receive the purified first portion of fluid for further purification of at least a second portion of the water.

3. Method for purifying water from a source comprising:
   a. passing water in a spiral fluid flow manner from the source through a first spiral wound reverse osmosis means being in fluid communication with the source so as to purify at least a first portion of the water from the source;
   b. passing the purified first portion of water through chemical means being in fluid communication with said first reverse osmosis means to receive said first purified portion of water and for removal of at least chemical contaminants from said first purified portions of water; and
   c. passing the chemically purified water in a spiral fluid flow manner through a second spiral wound reverse osmosis means being in fluid communication with said chemical means to receive the chemically purified water for purification of at least a second portion of the chemically purified water, said second reverse osmosis means also being in fluid communication with a first outlet and a second outlet so as to permit passage of said second portion of purified water through said first outlet and for passage of wastewater through said second outlet.

4. Method for purifying water from a source comprising:
   a. passing water in a spiral fluid flow manner from the source through a first spiral wound reverse osmosis means being in fluid communication with the source so as to purify at least a first portion of the water from the source;
   b. passing the purified first portion of water in a spiral fluid flow manner through a second spiral wound reverse osmosis means being in fluid communication with said first osmosis means to receive the purified first portion of water for further purification of at least a second portion of the water; and
   c. passing the purified second portion of water through chemical means being in fluid communication with said second reverse osmosis means to receive said second purified portion of water and for removal of at least chemical contaminants from said purified second portion of water, said chemical means also being in fluid communication with an outlet so as to permit passage of said chemically purified water through said outlet.

5. The method according to claim 4 further comprising passing the chemically purified water through a filtration means for further purification.

* * * * *